United States Patent
Gao et al.

(10) Patent No.: US 11,151,753 B2
(45) Date of Patent: Oct. 19, 2021

(54) GENERIC FRAMEWORK FOR BLURRING OF COLORS FOR TEETH IN GENERATED IMAGES USING HEIGHT MAP

(71) Applicant: Align Technology, Inc., San Jose, CA (US)

(72) Inventors: Yun Gao, Cary, NC (US); Yingjie Li, Cary, NC (US); Chao Shi, Morrisville, NC (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 16/579,673

(22) Filed: Sep. 23, 2019

(65) Prior Publication Data
US 2020/0105028 A1    Apr. 2, 2020

Related U.S. Application Data

(60) Provisional application No. 62/738,783, filed on Sep. 28, 2018.

(51) Int. Cl.
| | |
|---|---|
| *G06T 11/00* | (2006.01) |
| *G06T 7/70* | (2017.01) |
| *G06T 17/00* | (2006.01) |
| *G06T 19/20* | (2011.01) |
| *G06T 5/50* | (2006.01) |
| *G06T 5/00* | (2006.01) |
| *A61C 13/34* | (2006.01) |
| *A61C 9/00* | (2006.01) |
| *A61B 34/10* | (2016.01) |
| *G06T 7/50* | (2017.01) |

(52) U.S. Cl.
CPC ............ *G06T 11/001* (2013.01); *A61B 34/10* (2016.02); *A61C 9/0053* (2013.01); *A61C 13/34* (2013.01); *G06T 5/002* (2013.01); *G06T 5/005* (2013.01); *G06T 5/50* (2013.01); *G06T 7/50* (2017.01); *G06T 7/70* (2017.01); *G06T 17/00* (2013.01); *G06T 19/20* (2013.01); *A61B 2034/105* (2016.02); *A61C 2201/002* (2013.01); *G06T 2207/20084* (2013.01); *G06T 2207/30036* (2013.01); *G06T 2219/2016* (2013.01)

(58) Field of Classification Search
CPC combination set(s) only.
See application file for complete search history.

(56) References Cited

U.S. PATENT DOCUMENTS

| | | |
|---|---|---|
| 5,975,893 A | 11/1999 | Chishti et al. |
| 6,227,850 B1 | 5/2001 | Chishti et al. |

(Continued)

*Primary Examiner* — Sultana M Zalalee
(74) *Attorney, Agent, or Firm* — Lowenstein Sandler LLP

(57) ABSTRACT

A method includes determining depth values associated with a first set of pixel locations in a first image of a mouth. A first function is generated for a color channel based on intensities of the color channel at the first set of pixel locations and depth values associated with the first set of pixel locations. Image data comprising a new representation of the teeth is received, wherein the image data comprises a second set of pixel locations and new depth values associated with the second set of pixel locations. A new image is generated based on the image data and the first function, wherein a shape of the teeth is based on the image data and a color of the teeth is based on applying the first function to the second set of pixel locations for the teeth and the new depth values.

21 Claims, 17 Drawing Sheets

(56) References Cited

U.S. PATENT DOCUMENTS

| | | |
|---|---|---|
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 * | 11/2020 | Cramer ............... G06T 7/90 |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 2003/0008259 A1 | 1/2003 | Kuo et al. |
| 2003/0139834 A1* | 7/2003 | Nikolskiy ............. G16H 50/50 700/98 |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0020340 A1* | 1/2008 | Matov ............... A61C 7/08 433/24 |
| 2008/0306724 A1 | 12/2008 | Kitching et al. |
| 2008/0316209 A1* | 12/2008 | Wen ............... A61C 7/00 345/423 |
| 2009/0291417 A1* | 11/2009 | Rubbert ............... G06Q 10/06 433/215 |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2013/0286174 A1* | 10/2013 | Urakabe ............... A61B 1/247 348/66 |
| 2015/0089446 A1* | 3/2015 | James ............... G06F 3/04842 715/810 |
| 2016/0135925 A1 | 5/2016 | Mason et al. |
| 2016/0242870 A1 | 8/2016 | Matov et al. |
| 2016/0295191 A1* | 10/2016 | Babayoff ............. G01N 21/255 |
| 2016/0310235 A1 | 10/2016 | Derakhshan et al. |
| 2017/0143457 A1* | 5/2017 | Taub ............... A61C 13/0006 |
| 2017/0273760 A1 | 9/2017 | John et al. |
| 2018/0042698 A1* | 2/2018 | Salah ............... A61C 7/002 |
| 2018/0110590 A1* | 4/2018 | Maraj ............... A61C 13/0004 |
| 2018/0168775 A1 | 6/2018 | Derakhshan et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0076214 A1 | 3/2019 | Nyukhtikov et al. |
| 2019/0105127 A1 | 4/2019 | Velazquez et al. |
| 2019/0175303 A1 | 6/2019 | Akopov et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2019/0350680 A1 | 11/2019 | Chekh et al. |
| 2019/0357997 A1 | 11/2019 | Shi et al. |
| 2020/0000551 A1 | 1/2020 | Li et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0065997 A1* | 2/2020 | Lerch ............... A61C 19/10 |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0268495 A1* | 8/2020 | Ryakhovsky .......... A61C 7/002 |

(56) References Cited

U.S. PATENT DOCUMENTS

| | | |
|---|---|---|
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |

* cited by examiner

GENERIC FRAMEWORK FOR BLURRING OF COLORS FOR TEETH IN GENERATED IMAGES USING HEIGHT MAP

RELATED APPLICATIONS

This patent application claims the benefit under 35 U.S.C. § 119(e) of U.S. Provisional Application No. 62/738,783, filed Sep. 28, 2018.

TECHNICAL FIELD

Embodiments of the present disclosure relate to the field of dentistry and, in particular, to a system and method for generating simulated images of dental treatment outcomes with accurate coloration.

BACKGROUND

For both dental practitioners and patients who are considering undergoing orthodontic treatment it can be helpful to generate images that show what the patients' teeth will look like after treatment is performed. However, available techniques for generating simulated images that show orthodontic treatment outcomes of the patients' teeth are often unable to generate images with accurate coloration of the patients' teeth.

BRIEF DESCRIPTION OF THE DRAWINGS

Embodiments of the present disclosure are illustrated by way of example, and not by way of limitation, in the figures of the accompanying drawings.

DETAILED DESCRIPTION

Figure 1:
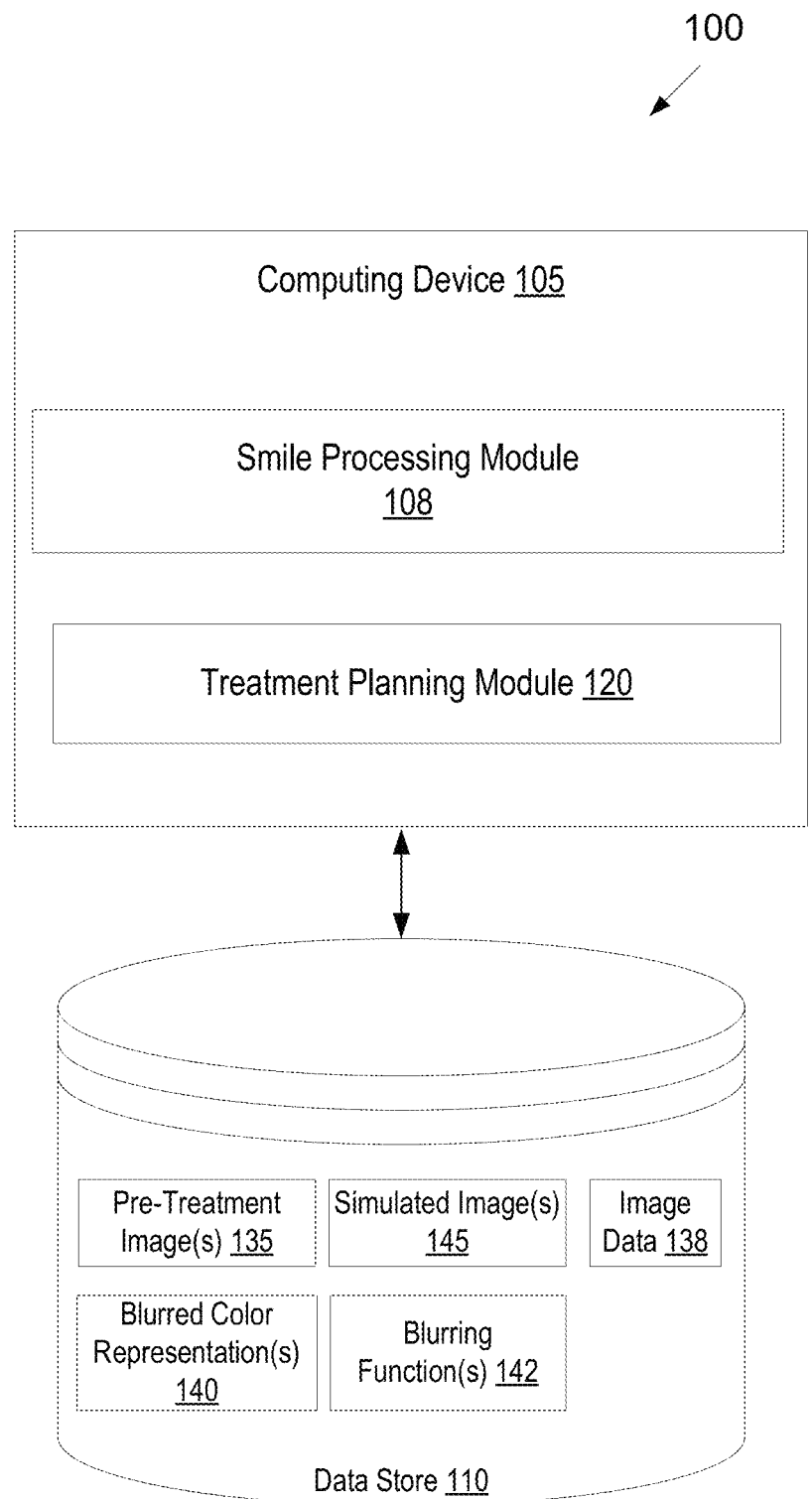
FIG. 1 illustrates one embodiment of a treatment planning system, in accordance with an embodiment.

Described herein are methods and systems for generating color data for use in the generation of accurate simulated images as well as methods and systems for generating such accurate simulated images based on the color data, in accordance with embodiments of the present disclosure. In some embodiments, the color data is a blurred color representation of a patient's teeth. The blurred color representation of the patient's teeth may be generated and combined with image data comprising a sketch or contours of the patient's teeth and/or gingiva to generate a realistic simulated image with accurate color data and accurate contours of the patient's teeth. The image data comprising the contours of the teeth and gingiva may be generated from a treatment plan (e.g., a simulated orthodontic treatment plan) and may show the contours of the teeth and gingiva after treatment has been performed. Embodiments enable an accurate simulated post-treatment image of a patient's smile to be generated based on a current image of the patient's smile as generated, for example, by a camera or image sensor. As used herein, simulated images include images that are not generated by image sensors.

Consumer smile simulations are simulated images generated for consumers (e.g., patients) that show how the smiles of those consumers will look after some type of dental treatment (e.g., such as orthodontic treatment). Clinical smile simulations are simulated images used by dental professionals (e.g., orthodontists, dentists, etc.) to make assessments on how a patient's smile will look after some type of dental treatment. For both consumer smile simulations and clinical smile simulations, a goal is to produce a post-treatment realistic photo rendering of a patient's smile that may be used by a patient, potential patient and/or dental practitioner to view a treatment outcome. For both use cases, the general process of generating the simulated image showing the post-treatment smile includes taking a picture of the patient's current smile, simulating or generating a treatment plan for the patient that indicates post-treatment positions and orientations for teeth and gingiva, and converting data from the treatment plan back into a new simulated image showing the post-treatment smile.

In some embodiments, current consumer and clinical smile simulations are generated by using a generative adversarial network (GAN) to texturize a rendered image (image data showing contours but possibly lacking color data such as color data for teeth) in order to produce realistic-looking teeth. To successfully texturize the rendered image and add accurate color data to the rendered image, a blurred color image and the image data showing the contours may be input to the GAN in order to generate the correct coloration for a particular individual. Other techniques for generating a blurred color representation of the teeth (e.g., such as Gaussian blurring) may generate spatially localized color data, which darkens areas of the blurred image where there were no teeth or where the teeth were recessed or discolored. This may result in the GAN producing tooth colorations for the rendered image that are also discolored causing the teeth to look either overly translucent or out of place.

In embodiments, global functions of the tooth coloration or intensity in a given color space are generated. The global functions may be, for example, parametric functions (e.g., polynomial functions such as biquadratic functions) and/or non-parametric functions (e.g., such as splines). Use of the global functions for tooth coloration results in a GAN texturization which is realistically colored in all regions of the rendered teeth. The global functions can be created using all points labeled as teeth in the original image in some embodiments. In further embodiments, the global functions may be created using an outlier removal algorithm, such as RANSAC.

In some embodiments, the global functions of the tooth coloration or intensity a functions of x,y pixel locations as well depth (z). Experimentation has shown that global blurring functions that use x,y pixel locations (but that omit depth information) produce simulated images of teeth in which the back molars are unnaturally bright or prominent. However, by using global functions that include both the x,y pixel locations as well as depth information, back molars in simulated images are natural and realistic.

Using a blurred color image (e.g., a blurred color representation of teeth and/or gingiva) as an input to the GAN to perform the texturing work causes the GAN to produce a photo-realistic post-treatment image of the smile with increased accuracy. Traditional blurring techniques are inherently local. However, the blurring techniques described in embodiments herein are global blurring techniques that result in improved realism and/or better image quality for simulated images (e.g., where tooth coloring appears more realistic and teeth appear straighter). The global blurring technique applied in embodiments a) is global across the teeth region in the mouth, b) identifies the proper color of each tooth even in areas where there are no current teeth, c) captures the color changes that occur naturally due to lighting changes and the location along the mouth arch, d) ignores local artifacts e) can be configured to work in the presence of noise by using outlier removal, f) does not produce back molars with unnatural prominence or luminance, and/or g) provides subtle depth change information for the teeth that causes simulated images to have natural curved surfaces and increases a 3D effect in simulated 2D images. Ultimately, the global blurring function described in embodiments enables a neural network such as a GAN to produce improved and more accurate texturing in simulated images of patient smiles.

In one embodiment, a processing device determines, from a first image of a mouth, a first region of the first image comprising a representation of teeth, wherein the first region comprises a first set of pixel locations in the first image. The processing device determines depth values associated with one or more of pixel locations in the first set of pixel locations. The depth information may be determined, for example, by generating a 3D model from the first image, determining points on the 3D model that map to pixel locations in the first image, and determining the depth information based on the z position of the points on the 3D model. Processing logic generates a first function for a first color channel based on a) intensities of the first color channel at the one or more pixel locations in the first set of pixel locations and b) depth values associated with the one or more pixel locations in the first set of pixel locations, wherein the first function comprises a first variable for a first image axis, a second variable for a second image axis and a third variable for a third image axis. Processing logic may also generate functions for one or more additional color channels.

Processing logic receives image data comprising a new representation of the teeth in a second region, wherein one or more of the teeth have a different position in the image data than in the first image, wherein the second region comprises a second set of pixel locations for the teeth that is different than the first set of pixel locations, and wherein the image data further comprises new depth values associated with pixel locations in the second set of pixel locations. The image data may be produced by simulating orthodontic treatment on the teeth in the 3D model to generate a new 3D model with straightened teeth, and then generating a new 2D image of the straightened teeth from the new 3D model as well as determining depth values for the pixel locations in the new 2D image from the new 3D model. The new 2D image may be a sketch or outline of the 3D model as viewed from a same perspective from which the first image was taken, and may lack color data in some embodiments. Processing logic generates a new image based on the image data and the first function for the first color channel (and optionally the one or more other functions for other color channels), wherein a shape of the teeth is based on the image data and a color of the teeth is based on applying the first function to the second set of pixel locations for the teeth and the new depth values associated with the second set of pixel locations for the teeth.

FIG. 1 illustrates one embodiment of a treatment planning system 100. In one embodiment, the treatment planning system 100 includes a computing device 105 and a data store 110. The treatment planning system 100 may additionally include, or be connected to, an image capture device such as a camera and/or an intraoral scanner. The computing device 105 may include physical machines and/or virtual machines hosted by physical machines. The physical machines may be rackmount servers, desktop computers, or other computing devices. The physical machines may include a processing device, memory, secondary storage, one or more input devices (e.g., such as a keyboard, mouse, tablet, speakers, or the like), one or more output devices (e.g., a display, a printer, etc.), and/or other hardware components. In one embodiment, the computing device 105 includes one or more virtual machines, which may be managed and provided by a cloud provider system. Each virtual machine offered by a cloud service provider may be hosted on one or more physical machine. Computing device 105 may be connected to data store 110 either directly or via a network. The network may be a local area network (LAN), a public wide area network (WAN) (e.g., the Internet), a private WAN (e.g., an intranet), or a combination thereof.

Data store 110 may be an internal data store, or an external data store that is connected to computing device 105 directly or via a network. Examples of network data stores include a storage area network (SAN), a network attached storage (NAS), and a storage service provided by a cloud provider system. Data store 110 may include one or more file systems, one or more databases, and/or other data storage arrangement.

The computing device 105 may receive one or more images from an image capture device or from multiple image capture devices. The image capture device may be or include a charge-coupled device (CCD) sensor and/or a complementary metal-oxide semiconductor (CMOS) sensor. The image capture device may provide images or video to the computing device 105 for processing. For example, the image capture device 160 may provide images to the computing device 105 that the computing device analyzes to identify a patient's mouth, a patient's face, a patient's dental arch, or the like. In some embodiments, the images captured by image capture device may be stored in data store 110 as pre-treatment images 135. For example, pre-treatment images 135 may be stored in data store 110 as a record of patient history or for computing device 105 to use for analysis of the patient and/or for generation of simulated post-treatment images. The image capture device may transmit the discrete images and/or video to the computing device 105, and computing device 105 may store the pre-treatment images 135 in data store 110. In some embodiments, the pre-treatment images 135 include two-dimensional data.

Computing device 105 includes a smile processing module 108 and a treatment planning module 120 in embodiments. The treatment planning module 120 is responsible for generating a treatment plan that includes a treatment outcome for a patient. The treatment plan may be a simulated treatment plan that includes and/or is based on an initial 2D and/or 3D image of the patient's dental arches. For example, the treatment planning module 120 may receive 3D intraoral images of the patient's dental arches, and may stitch the 3D images together to create a virtual 3D model of the dental arches. Alternatively, the treatment planning module 120 may receive an initial 2D image, and may generate a virtual 3D model from the initial 2D image. The treatment planning module 120 may then determine current positions and orientations of the patient's teeth from the virtual 3D model and determine target final positions and orientations for the patient's teeth represented as a treatment outcome. The treatment planning module 120 may then generate a virtual 3D model showing the patient's dental arches at the end of treatment as well as one or more virtual 3D models showing the patient's dental arches at various intermediate stages of treatment. Alternatively, or additionally, the treatment planning module 120 may generate one or more 3D images and/or 2D images showing the patient's dental arches at various stages of treatment.

By way of non-limiting example, a treatment outcome may be the result of a variety of dental procedures. Such dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as implants, crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances. Any of treatment outcomes or updates to treatment outcomes described herein may be based on these orthodontic and/or dental procedures. Examples of orthodontic treatments are treatments that reposition the teeth, treatments such as mandibular advancement that manipulate the lower jaw, treatments such as palatal expansion that widen the upper and/or lower palate, and so on. For example, an update to a treatment outcome may be generated by interaction with a user to perform one or more procedures to one or more portions of a patient's dental arch or mouth. Planning these orthodontic procedures and/or dental procedures may be facilitated by the AR system described herein.

A treatment plan for producing a particular treatment outcome may be generated by first generating an intraoral scan of a patient's oral cavity. From the intraoral scan a virtual 3D model of the upper and/or lower dental arches of the patient may be generated. A dental practitioner may then determine a desired final position and orientation for the patient's teeth on the upper and lower dental arches, for the patient's bite, and so on. This information may be used to generate a virtual 3D model of the patient's upper and/or lower arches after orthodontic treatment. This data may be used to create an orthodontic treatment plan. The orthodontic treatment plan may include a sequence of orthodontic treatment stages. Each orthodontic treatment stage may adjust the patient's dentition by a prescribed amount, and may be associated with a 3D model of the patient's dental arch that shows the patient's dentition at that treatment stage.

A simulated treatment plan may additionally or alternatively be generated based on an initial 2D image of a patient's open-mouthed smile. A 3D model may be generated from the initial 2D image, and a dental practitioner or automated treatment planning software may determine a desired final position and orientation for the patient's teeth on the upper and lower dental arches, for the patient's bite, and so on. This information may be used to generate a new virtual 3D model of the patient's upper and/or lower arches after orthodontic treatment.

In some embodiments, the treatment planning module 120 may receive or generate one or more virtual 3D models, virtual 2D models, 3D images, 2D images, or other treatment outcome models and/or images based on received intraoral images. For example, an intraoral scan of the patient's oral cavity may be performed to generate an initial virtual 3D model of the upper and/or lower dental arches of the patient. Treatment planning module 120 may then determine a final treatment outcome based on the initial virtual 3D model, and then generate a new virtual 3D model representing the final treatment outcome.

Smile processing module 180 may generate simulated post-treatment images of patient smiles. To generate a simulated post-treatment image, smile processing module 180 generates one or more blurring functions. This may include setting up the functions, and then solving for the one or more blurring functions using data from an initial pre-treatment image 135. In some embodiments, a first set of blurring functions is generated (e.g., set up and then solved for) with regards to a first region depicting teeth in the pre-treatment image 135 and a second set of blurring functions is generated with regards to a second region depicting gingiva in the pre-treatment image 135. Once the blurring functions are generated, these blurring functions may be applied to image data such as sketches depicting contours of the teeth and/or gingiva post-treatment. For example, the blurring functions for the teeth may be applied to a third region depicting the teeth in a post-treatment sketch and the blurring functions for the gingiva may be applied to a fourth region depicting the gingiva in the post-treatment sketch.

In embodiments, the blurring functions for the teeth and/or gingiva are global blurring functions that are parametric functions or non-parametric functions. Examples of parametric functions that may be used include polynomial functions (e.g., such as biquadratic functions), trigonometric functions, exponential functions, fractional powers, and so on. Examples of non-parametric functions that may be used include splines such as cubic splines or natural splines. In one embodiment, a set of parametric and/or non-parametric functions are generated that will function as a global blurring mechanism for a patient. The functions may be unique functions generated for a specific patient based on an image of that patient's smile. Each function may be based on two-dimensional (2D) pixel locations as well as depth values associated with those 2D pixel locations. A set of functions (one per color channel of interest) may be generated, where each function provides the intensity, I, for a given color channel, c, at a given pixel location (x,y) and a given depth (z) according to one of the following equations:

$$I_c(x,y,z) = f(x,y) + g(z) \quad (1a)$$

$$I_c(x,y,z) = f(x,y)g(z) \quad (1b)$$

As shown in equations 1a-1b above, the function for a color channel may include two sub-functions f(x,y) and g(z). The interaction between these two sub-functions can be modeled as an additive interaction (as shown in equation 1a) or as a multiplicative interaction (as shown in equation 1b). If the interaction effect between the sub-functions is multiplicative, then the rate of change of the intensity also depends on the 2D location (x,y). Functions f(x,y) and g(z) may both be parametric functions or may both be non-parametric functions. Additionally, a first one of function f(x,y) and g(z) may be a parametric function and a second of f(x,y) and g(z) may be a non-parametric function. In an example, the intensity I (or lightness L) may be set up as a random variable with Gaussian distribution, with a conditional mean being a function of x, y and z.

Figure 10A:
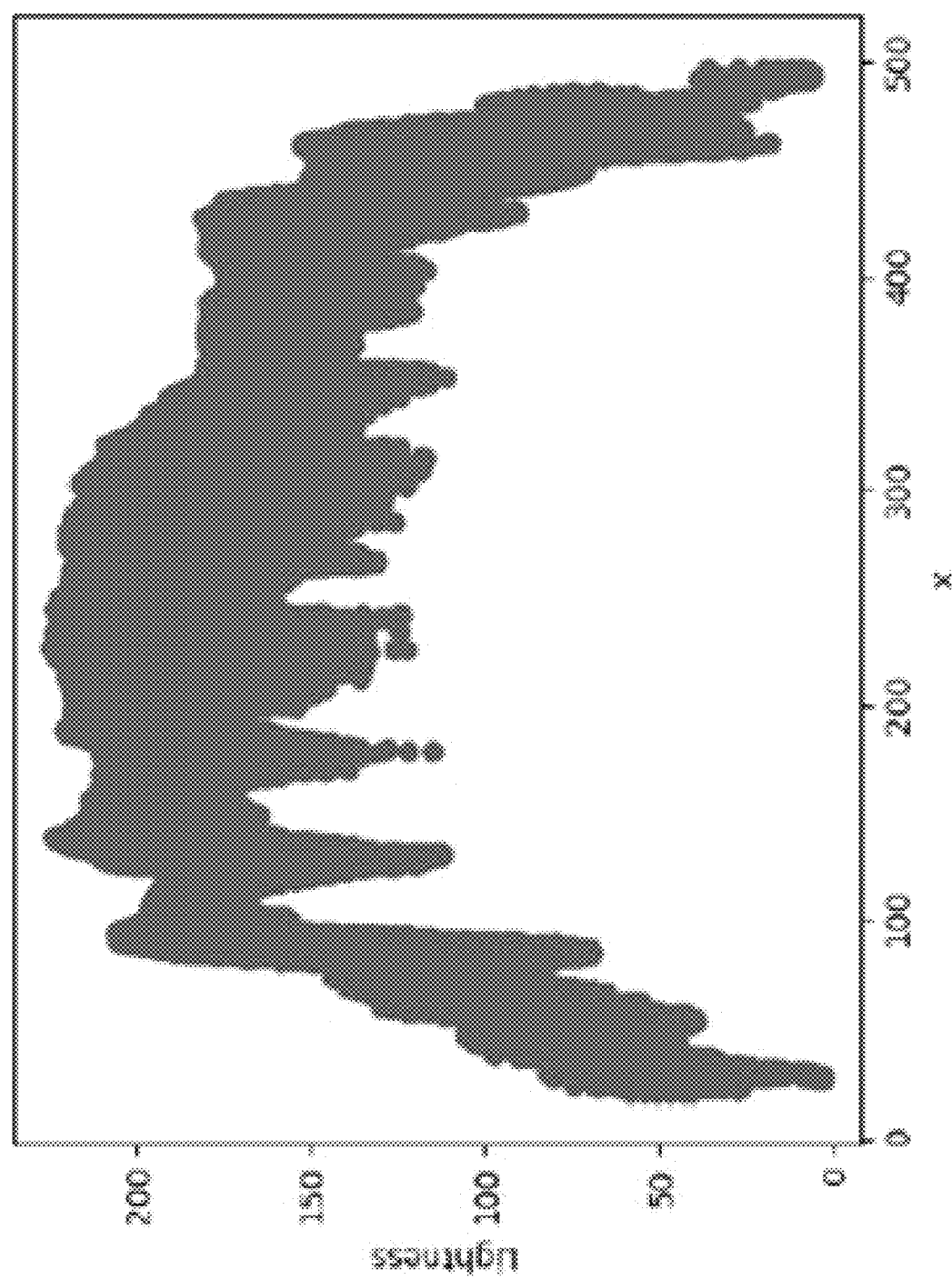
FIG. 10A is an example scatter plot showing lightness variation along an x-axis, in accordance with an embodiment.
Figure 10B:
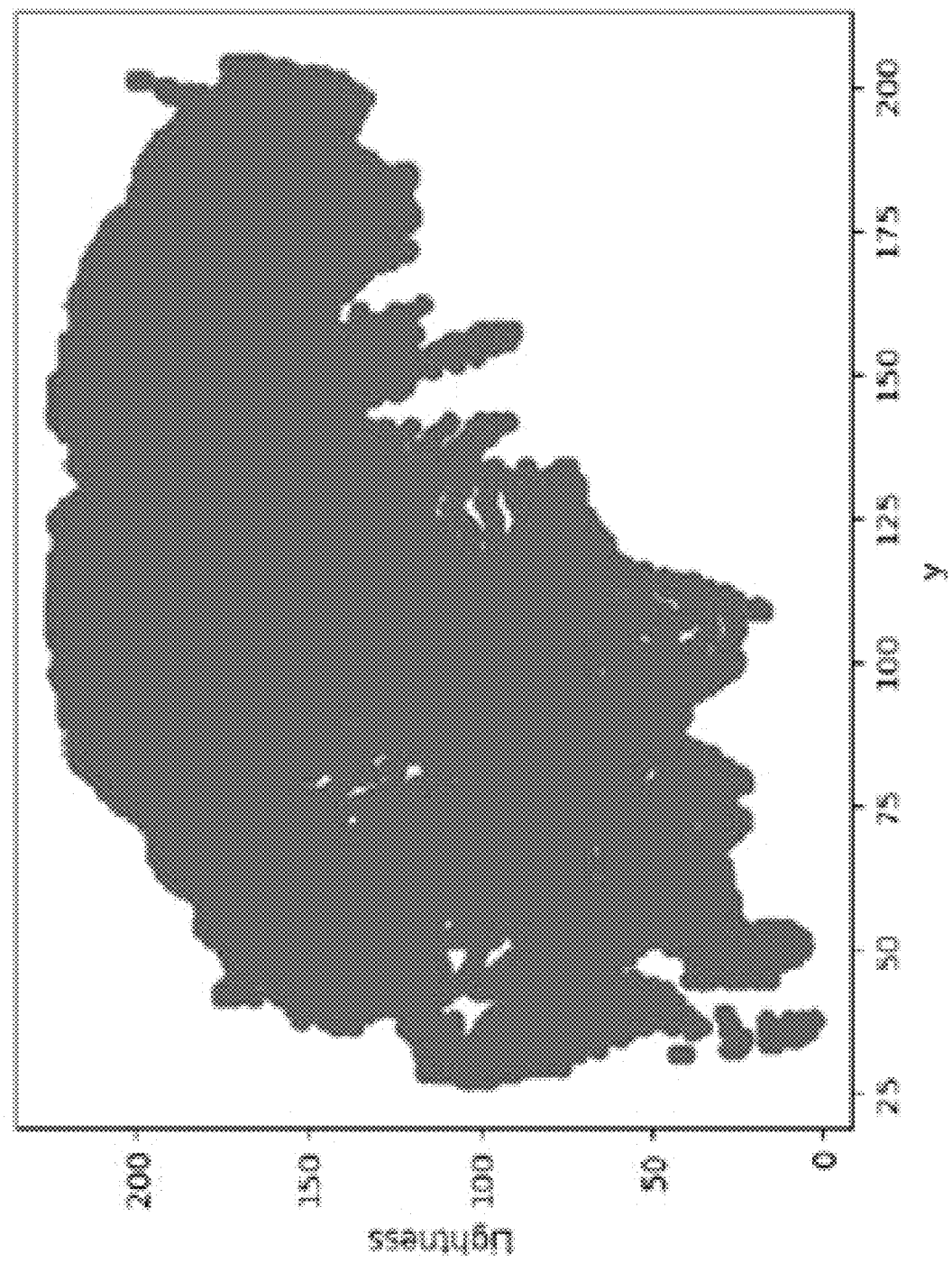
FIG. 10B is an example scatter plot showing lightness variation along a y-axis, in accordance with an embodiment.
Figure 10C:
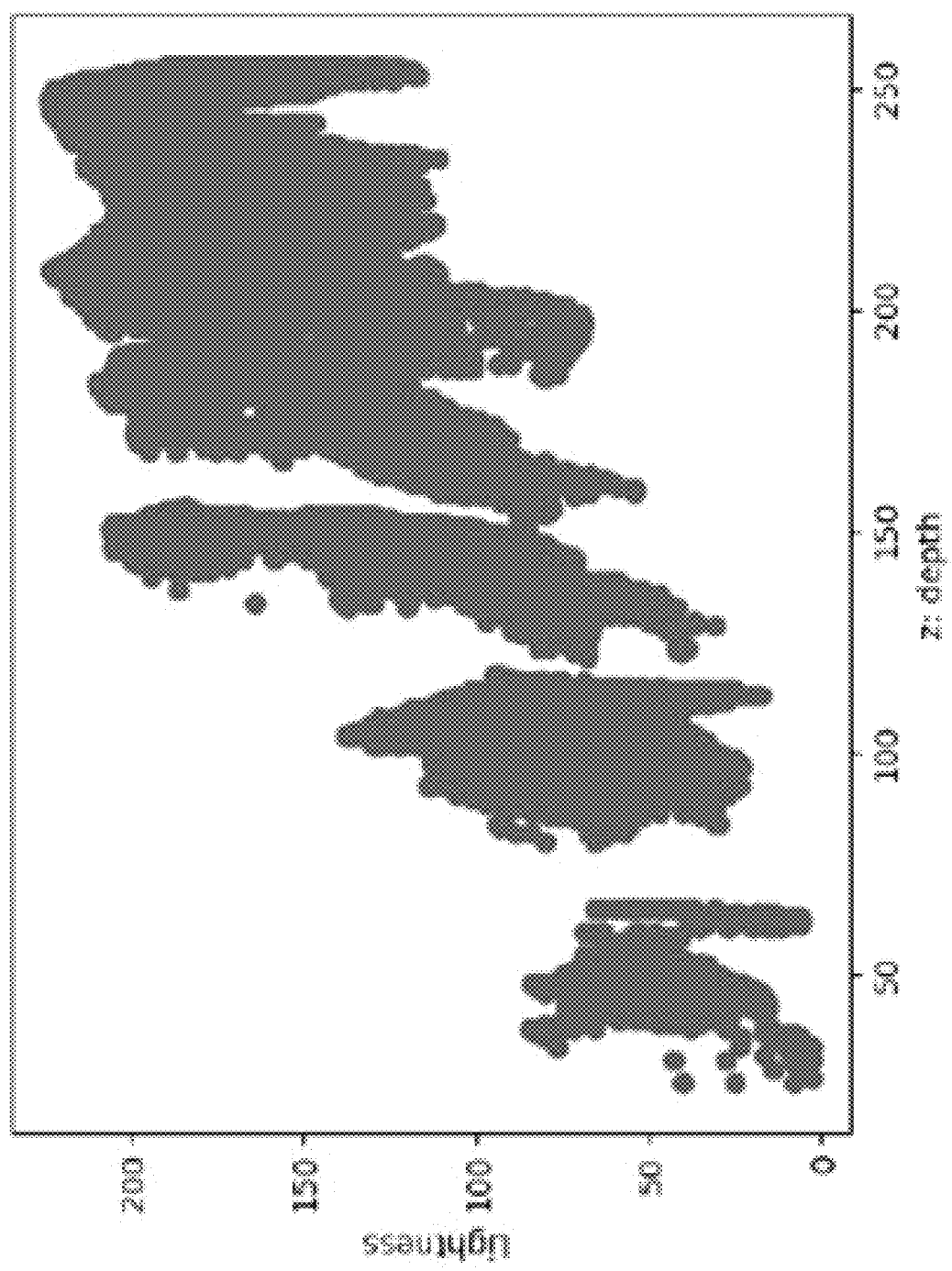
FIG. 10C is an example scatter plot showing lightness variation along a z-axis, in accordance with an embodiment.

In one embodiment, the LAB color space is used, and lightness (L) is modeled as a function of 2D location (x,y) and depth (z). For example, an initial image may be generated in the RGB color space and may be converted to the LAB color space. FIG. 10A illustrates a scatter plot of lightness against x. As shown in FIG. 10A, the teeth are brighter near the center along the x-axis. FIG. 10B illustrates a scatter plot of lightness against y. As shown in FIG. 10B, there is little correlation between position along the y-axis and lightness. FIG. 10C illustrates a scatter plot of lightness against z. As shown in FIG. 10C, the teeth are progressively darker with increases in depth (z). Accordingly, there is a strong correlation between depth and lightness and/or intensity.

In one embodiment, RGB is modeled as a second degree polynomial of (x,y) pixel location. In one embodiment, for depth (z), lightness (L) is modeled as a function of x, y and z. Color channels may be kept as in the above second degree polynomial.

The sub-functions may be combined and converted to the RGB color space. The sub-functions may be set up as polynomials of varying degree and/or as other parametric functions or non-parametric functions. Additionally, multiple different interaction effects between the sub-functions may be modeled (e.g., between f(x,y) and g(z)). Accordingly, in one embodiment the lightness L may be modeled according to one of the following equations:

$$E[L|(x,y,z)] = f(x,y) + g(z) \quad (2a)$$

$$E[L|(x,y,z)] = f(x,y)g(z) \quad (2b)$$

where E is the expectation or mean.

There are multiple different functions that may be used for f and g above, and these functions may be combined in multiple different ways. In one embodiment, f is modeled as a second degree polynomial and g is modeled as a linear function, as follows:

$$f(x,y) = a_0 + a_1 x^2 + a_2 y^2 \quad (3)$$

$$g(z) = b_0 + b_1 z \quad (4)$$

where $a_0$, $a_1$, $a_2$, $b_0$ and $b_1$ are coefficients (parameters) for each term of the functions, x is a variable representing a location on the x axis, y is a variable representing a location on the y axis (e.g., x and y coordinates for pixel locations, respectively), and z is a variable representing depth (e.g., location on the z axis).

A multiplicative combination of these functions results in:

$$I_c(x,y,z) = w_0 + w_1 x^2 + w_2 y^2 + w_3 x^2 z + w_4 y^2 z \quad (5)$$

An additive combination of these functions results in:

$$I_c(x,y,z) = w_0 + w_1 x^2 + w_2 y^2 + w_3 z \quad (6)$$

where $w_0$ may be equal to $a_0 + b_0$, $w_1$ may be equal to $a_1$, $w_2$ may be equal to $a_2$ and $w_3$ may be equal to $b_1$.

These embodiments result in stable models that are efficient and fast to solve for.

If the function is a parametric function, then it may be solved using linear regression (e.g., multiple linear regression). Some example techniques that may be used to perform the linear regression include the ordinary least squares method, the generalized least squares method, the iteratively reweighted least squares method, instrumental variables regression, optimal instruments regression, total least squares regression, maximum likelihood estimation, rigid regression, least absolute deviation regression, adaptive estimation, Bayesian linear regression, and so on.

To solve the parametric function, a mask M of points may be used to indicate those pixel locations in the initial image that should be used for solving the parametric function. For example, the mask M may specify some or all of the pixel locations that represent teeth in the image if the parametric function is for blurring of teeth or the mask M may specify some or all of the pixel locations that represent gingiva if the parametric function is for the blurring of gingiva.

If the function is a non-parametric function, then it may be solved using back-fitting. To perform back-fitting, both functions f and g are initial set as constant functions. Then processing logic iterates between fixing a first function, and fitting the residual $L-\hat{L}$ against the second function. Then alternating and fixing the second function and fitting the residual $L-\hat{L}$ against the first function. This may be repeated one or more times until the residual falls below some threshold.

Figure 11:
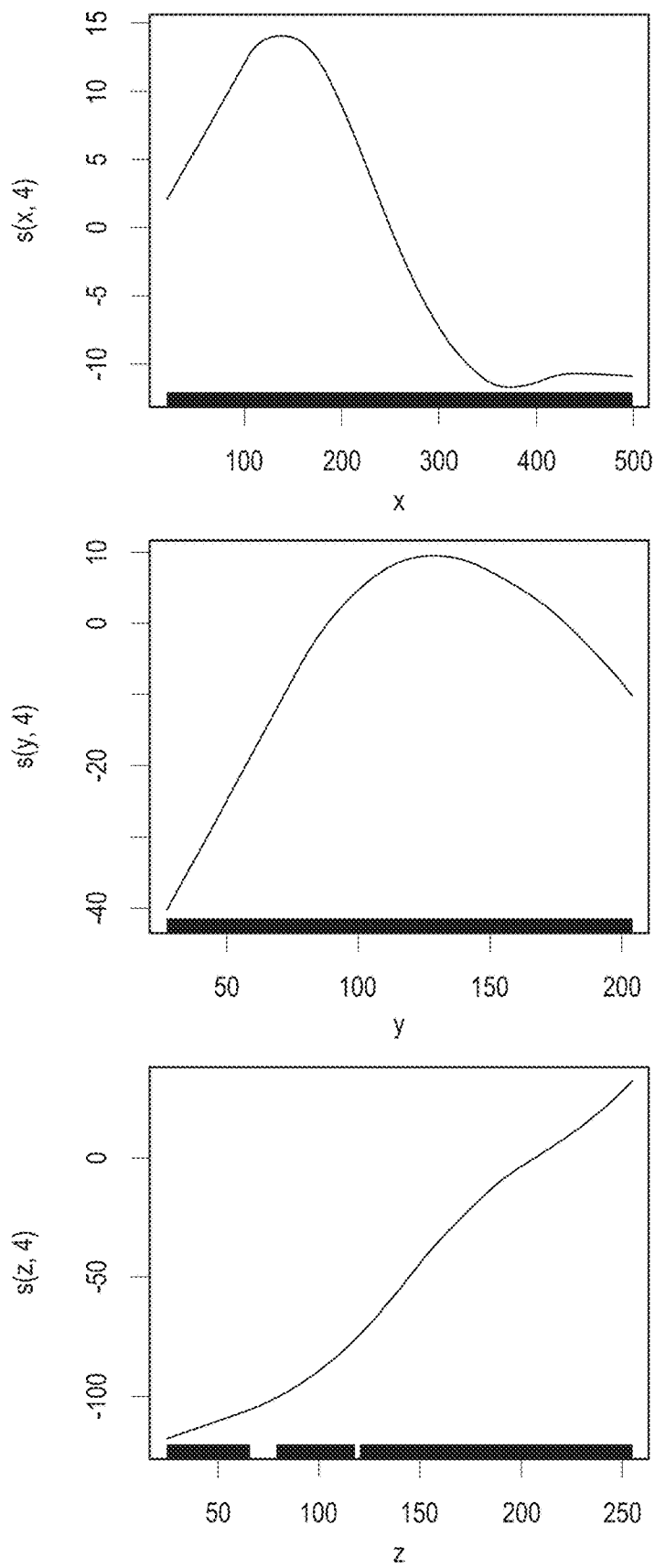
FIG. 11 shows plots for x, y and z that include fitted splines.

An example non-parametric function that may be used is a spline, such as a smoothing spline. Non-parametric models like natural splines have local support and are more stable than high degree polynomials. However, the fitting process for non-parametric functions takes longer and uses more computing resources than the fitting process for parametric functions. In one embodiment, the package gam available in R is used to fit a smoothing spline with degree of freedom 4 to each variable (x,y,z). FIG. 11 shows plots for x, y and z that include fitted splines. The output below shows the fitting details, which shows all the terms are significant.

```
Call: gam(formula = val ~ s(x, 4) + s(y, 4) + s(z, 4), data = data)
Deviance Residuals:
     Min        1Q     Median       3Q        Max
 -100.295    -7.859     1.997     10.448     71.771
(Dispersion Parameter for gaussian family taken to be 291.8699)
Null Deviance: 78650387 on 48900 degrees of freedom
Residual Deviance: 14268936 on 48888 degrees of freedom
AIC: 416367.2
Number of Local Scoring Iterations: 6
Anova for Parametric Effects
          Df    Sum Sq    Mean Sq    F value    Pr(>F)
s(x, 4)    1    207988    207988     712.61    <2.2e-16 ***
s(y, 4)    1   6796471   6796471   23285.96    <2.2e-16 ***
s(z, 4)    1  45906457  45906457  157283.96    <2.2e-16 ***
Residuals 48888  14268936    292

Signif. codes: 0 '***' 0.001 '**' 0.01 '*' 0.05 '.' 0.1 ' ' 1
Anova for Nonparametric Effects
          Npar Df Npar F    Pr(F)
(Intercept)
s(x, 4)      3   1733.2   <2.2e-16 ***
s(y, 4)      3   3866.0   <2.2e-16 ***
s(z, 4)      3   1033.6   <2.2e-16 ***

Signif. codes: 0 '***' 0.001 '**' 0.01 '*' 0.05 '.' 0.1 ' ' 1
```

Figure 12:
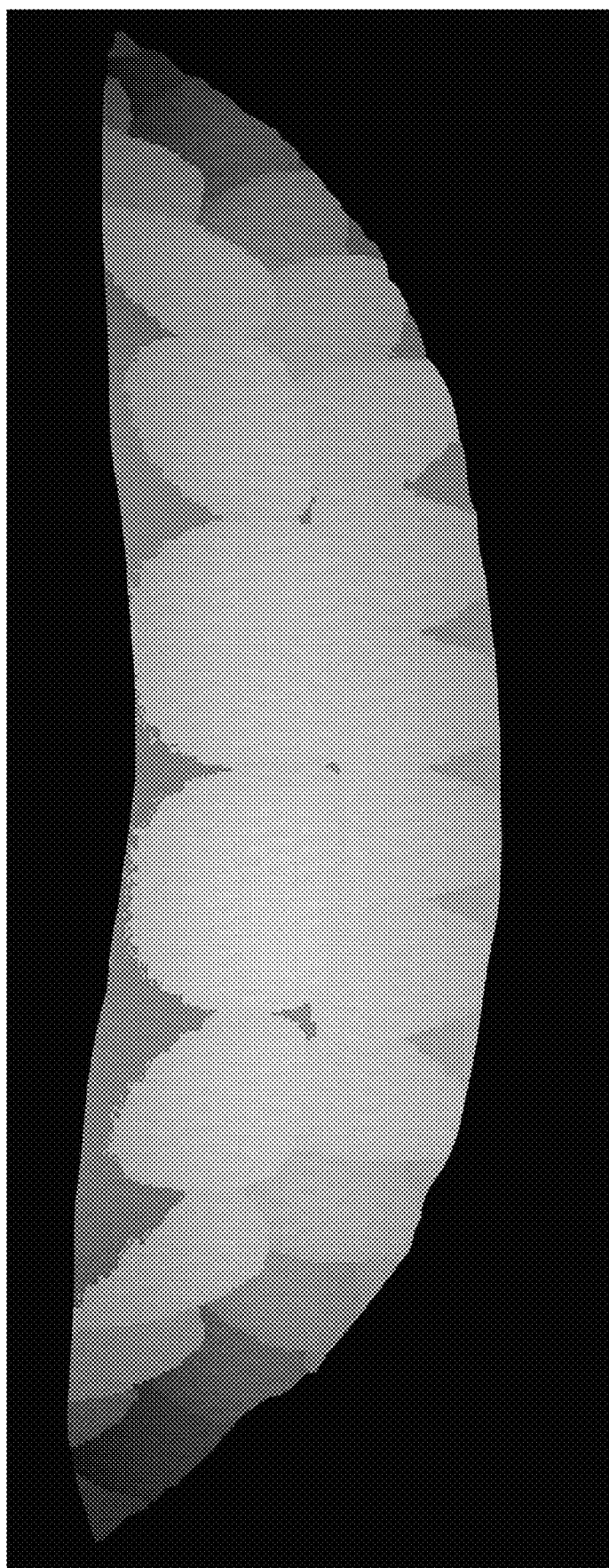
FIG. 12 illustrates a blurry image generated using the smoothing spline functions solved for with reference to FIG. 11.

FIG. 12 illustrates a blurry image generated using the smoothing spline functions solved for with reference to FIG. 11.

Figure 13A:
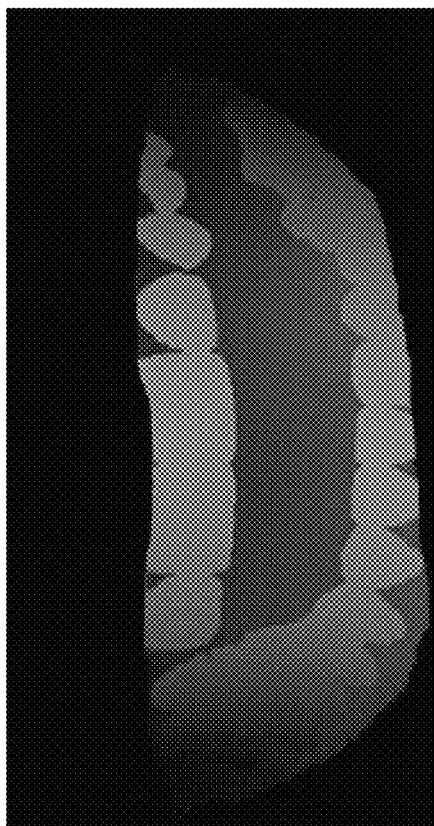
FIG. 13A illustrates a blurry image generated using a blurring function that does not take depth into account.
Figure 13B:
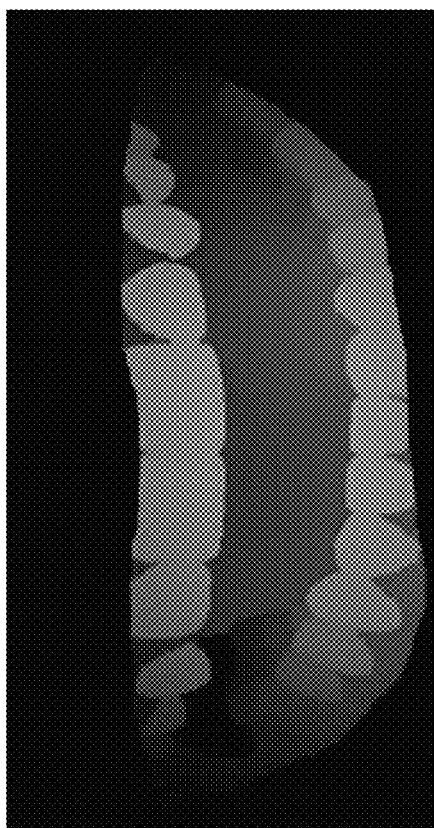
FIG. 13B illustrates a blurry image generated using a blurring function that does take depth into account.
Figure 13C:
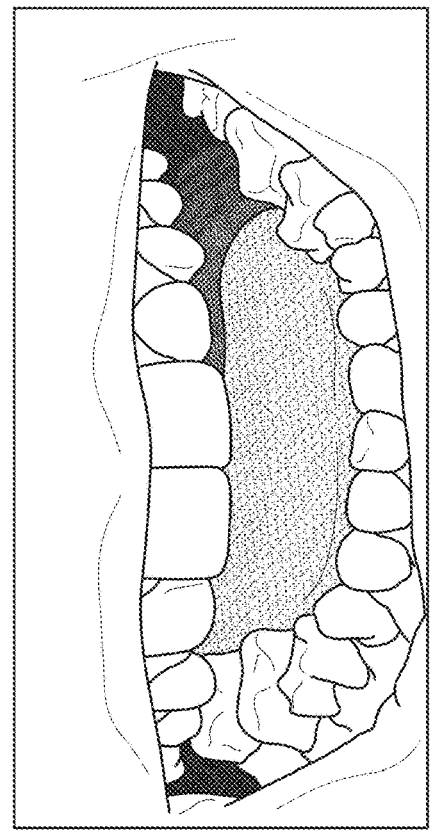
FIG. 13C illustrates a simulated image generated based on the blurry image of FIG. 13A.
Figure 13D:
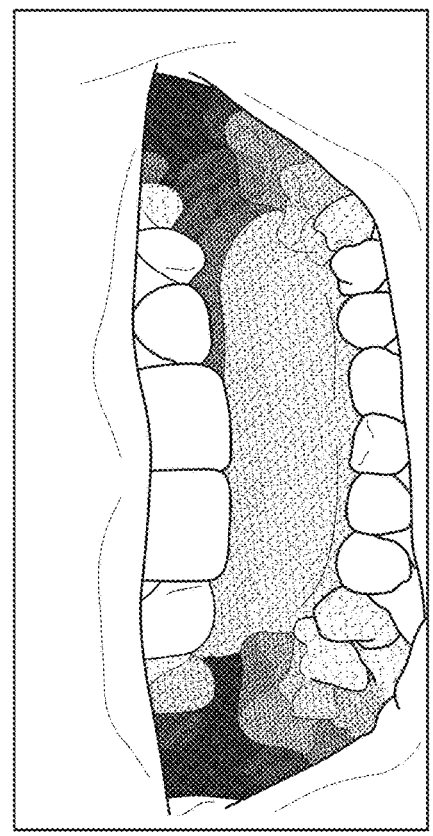
FIG. 13D illustrates a simulated image generated based on the blurry image of FIG. 13B.

FIG. 13A illustrates a blurry image generated using a blurring function that does not take depth into account. FIG. 13B illustrates a blurry image generated using a blurring function that does take depth into account. FIG. 13C illustrates a simulated image generated based on the blurry image of FIG. 13A. FIG. 13D illustrates a simulated image generated based on the blurry image of FIG. 13B. As shown, the simulated image in FIG. 13A includes prominent molars, whereas the simulated image in FIG. 13D includes a more realistic image of a smile with less prominent molar.

In one embodiment, by constructing blurring functions (e.g., parametric blurring functions) separately for the teeth and the gum regions, a set of color channels can be constructed that avoid any pattern of dark and light spots that may have been present in the initial image as a result of shading (e.g., because one or more teeth were recessed).

In embodiments, the blurring functions for the gingiva are local blurring functions such as Gaussian blurring functions. A Gaussian blurring function in embodiments has a high radius (e.g., a radius of at least 5, 10, 20, 40, or 50 pixels). The Gaussian blur may be applied across the mouth region of the initial image in order to produce color information. A Gaussian blurring of the image involves convolving a two-dimensional convolution kernel over the image and producing a set of results. Gaussian kernels are parameterized by $\sigma$, the kernel width, which is specified in pixels. If the kernel width is the same in the x and y dimensions, then the Gaussian kernel is typically a matrix of size $6\sigma+1$ where the center pixel is the focus of the convolution and all pixels can be indexed by their distance from the center in the x and y dimensions. The value for each point in the kernel is given as:

$$G(x, y) = \frac{1}{2\pi\sigma^2} e^{-\frac{x^2+y^2}{2x^2}} \quad (7)$$

In the case where the kernel width is different in the x and y dimensions, the kernel values are specified as:

$$G(x, y) = G(x)G(y) = \frac{1}{2\pi\sigma_x\sigma_y} e^{-\left(\frac{x^2}{2\sigma_x^2} + \frac{y^2}{2\sigma_y^2}\right)} \quad (8)$$

One problem with using color channels produced via a Gaussian blurring function is that they maintain some structure in the very color they represent. In particular, one can see brighter and darker regions in the blurred image. When a trained neural network (e.g., a GAN model) attempts to color a sketch of the correctly positioned post-treatment teeth, the regions of light and dark from the original image may remain, causing the teeth to look discolored or possibly out of alignment. Accordingly, in embodiments the Gaussian blurring function is used to generate a blurred color representation of gingiva but not of teeth. In other embodiments, the Gaussian blurring function is used to generate a blurred color representation of the teeth.

In some embodiments, the blur produced by the blurring functions is sufficiently great that the tooth structure is not readily apparent to a human observer. Alternatively, the tooth structure may be apparent in the blurred image, such as in the blurred image of FIG. 12. The post treatment sketch and a blurred color image comprising a blurred color representation of the gingiva and a blurred color representation of the teeth may then be used together to generate a photo-realistic simulated post-treatment image of the patient's smile. Color data for the simulated image of the post-treatment smile may be based on the blurred color image and the shape of the teeth and gingiva in the simulated image may be based on the post-treatment image data (e.g., a sketch of the teeth and gingiva as they will appear after treatment).

In some embodiments, neural networks, such as generative adversarial networks (GANs), conditional GANs or picture to picture GANs may be used to generate a post-treatment image of a smile having teeth in a final treatment position. The neural network may integrate data from a 3D model of an upper and/or lower dental arch with teeth in a final position with blurred color image of the patient's smile. The blurred color image of the patient's smile may be generated by applying one or more generated blurring functions to the data from the 3D model as described above. The data may be received as 3D data or as 2D data (e.g., as a 2D view of a 3D virtual model of the patient's dental arch). The neural network may use the input data to generate a simulated post-treatment image that matches the colors, tones, shading, etc. from the blurred color image with the shape and contours of the teeth and gingiva from the post treatment image data (e.g., data from the 3D model).

The neural network may have been trained using a training dataset comprising facial images (e.g., images of smiles showing teeth and gingiva), sketches associated with the facial images (e.g., showing contours of the facial images but possibly lacking color data) and blurred color images comprising color data associated with the facial images. In some embodiments, the facial images are the target and the sketches and blurred color inputs are the inputs used for training the neural network. The neural network may be trained to generate a photo-realistic image of a smile based on a combined input that includes a blurred color image that lacks structural data and a sketch that has structural data but may lack color data. The neural network may also be trained to identify teeth and their contours. For example, each tooth may be identified by type (e.g., upper left central incosor, lower right canine). The neural network may also be trained to identify other aspects and features during training, such as the location and color of the gingiva, the color of the teeth, the relative brightness of the surfaces within the mouth, and others.

After training, the neural network receives inputs for use in generating a realistic rendering of the patient's teeth in a clinical final position. In order to provide color information to the GAN model, a blurred color image that represents a set of color channels is provided along with a post-treatment sketch of teeth and/or gingiva for a patient. The color channels are based on the initial photo and contain information about the color and lighting of the teeth and/or gums in that initial image. In order to avoid sub-optimal results from the GAN model, no structural information (e.g., tooth location, shape, etc.) remains in the blurred color image in embodiments.

As discussed above, the inputs may include a blurred color image of the patient's teeth and gingiva as well as an image (e.g., a sketch) of teeth and/or gingiva in a clinical final position (e.g., a 2D rendering of a 3D model of the patient's teeth in the clinical final position), a 3D rendered model of the patients teeth in the clinical final position, and so on. The clinical final position may have been determined, for example, according to an orthodontic treatment plan.

The neural network uses the inputs and a set of trained model parameters to render a realistic image of the patient's teeth in a final position. This photo realistic image is then integrated into the mouth opening of the facial image and an alpha channel blurring may be applied. Returning to FIG. 1, in embodiments, the smile processing module 108 provides a significantly more realistic integration of the post treatment tooth and gingiva positions and shapes taken from the treatment plan with actual colors of the patient's teeth and gingiva.

In embodiments, pre-treatment images 135, simulated images 145, image data 138, blurred color representations 140 and blurring functions 142 may be stored in a data store 110 (or in separate data stores). Additionally, one or more virtual 3D models (e.g., representing a patient's current dentition and/or a patient's target final dentition) may be stored in the data store 110. For example, pre-treatment images 135, simulated images 145, image data 138 and blurred color representations 140 may be stored as entries in the same database or in separate databases. In an example, a database may contain separate entries for each x,y pixel location and associated depth (z) value of a pre-treatment image 135. An entry may include a value for an x coordinate, a value for a y coordinate, a depth (z) value, values for each of the color channels of a color space at the x,y location, a value indicating whether the x,y pixel location is associated with a tooth region or a gingiva region, and so on. Operations performed by the smile processing module 108 to generate blurring functions 142, to generate blurred color representations 140 and/or to generate simulated images 145 may be performed as mathematical operations between different database entries in the data store 110 (or multiple data stores).

FIGS. 2A-4 below describe methods of generating blurring functions and using the blurring functions to generate simulated images of a patient's smile with accurate color data. The blurring functions are stable and apply accurately to all types of lighting conditions. Additionally, the blurring functions are usable to generate simulated images that include subtle shades between teeth and within teeth and that show an apparent 3D effect in the output 2D images. The methods depicted in FIGS. 2A-4 may be performed by a processing logic that may comprise hardware (e.g., circuitry, dedicated logic, programmable logic, microcode, etc.), software (e.g., instructions run on a processing device), or a combination thereof. Various embodiments may be performed by a computing device 105 as described with reference to FIG. 1.

Figure 2A:
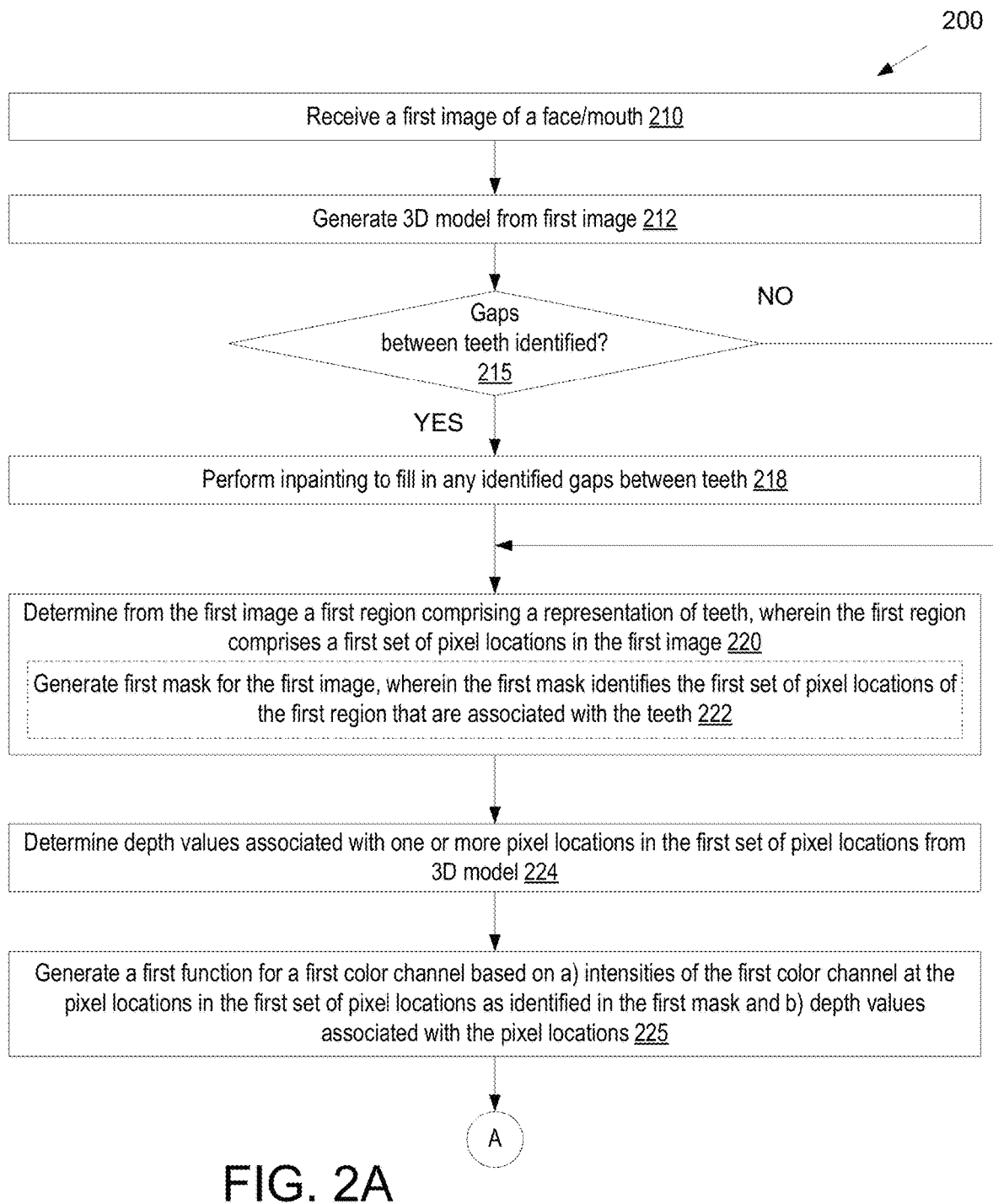
FIGS. 2A-B illustrate a flow diagram for a method of generating simulated images of dental treatment outcomes, in accordance with an embodiment.
Figure 2B:
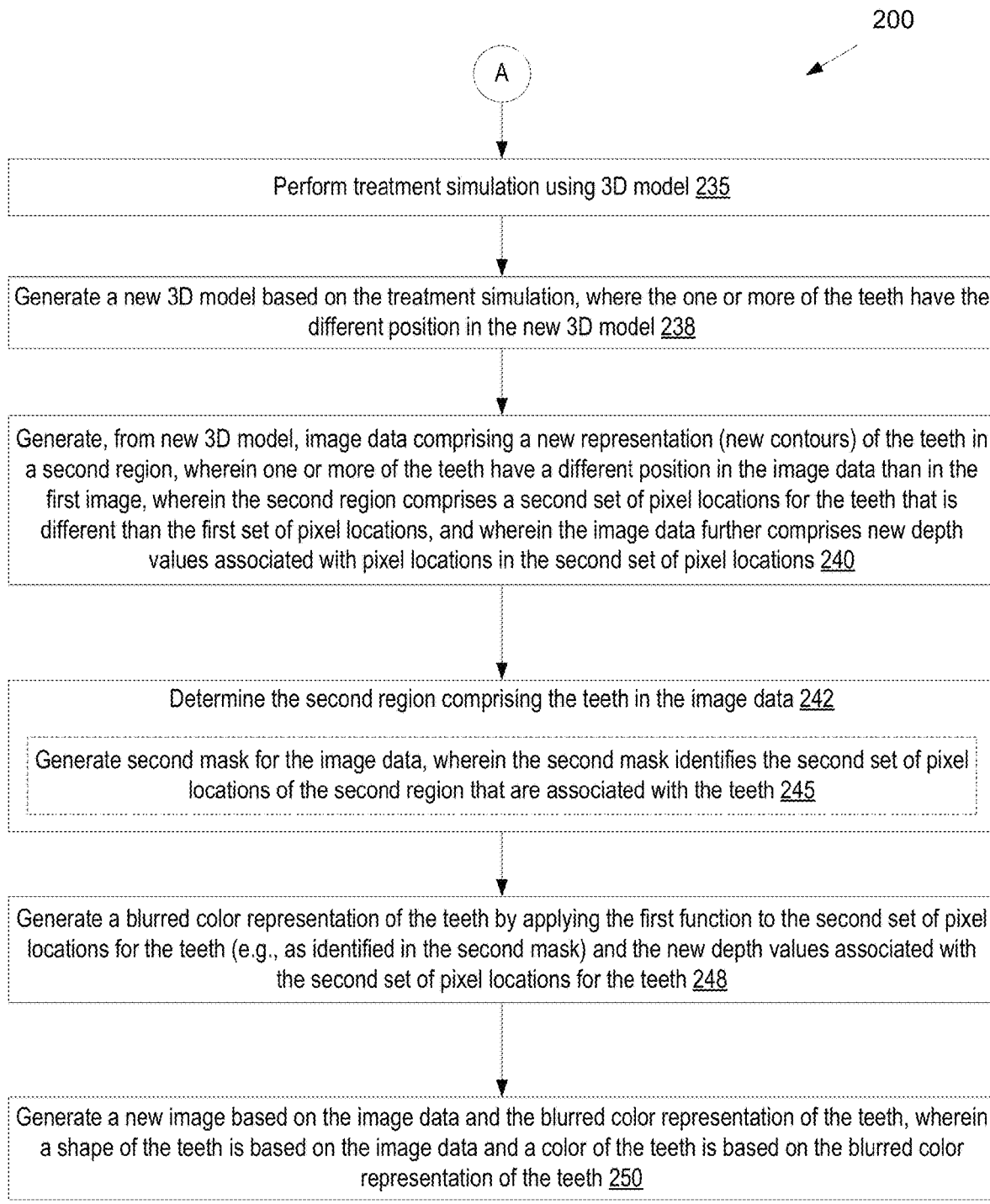

FIGS. 2A-B illustrate a flow diagram for a method 200 of generating simulated images of dental treatment outcomes, in accordance with an embodiment. At block 210 of method 200, processing logic receives a first image of a patient's face and/or mouth. The image may be an image of the patient smiling with their mouth open such that the patient's teeth and gingiva are showing. The first image may be a two-dimensional (2D) color image in embodiments.

At block 212, processing logic may generate a 3D virtual model of the patient's dental arches (e.g., including teeth and/or gums) from the 2D image. At block 215, processing logic determines whether there are any gaps between teeth. Such gaps may include gaps between adjacent teeth in the upper or lower dental arches and/or gaps between teeth in the upper arch and opposing teeth in the lower arch. If one or more gaps are identified, the method proceeds to block 218. Otherwise, the method continues to block 220.

Figure 9:
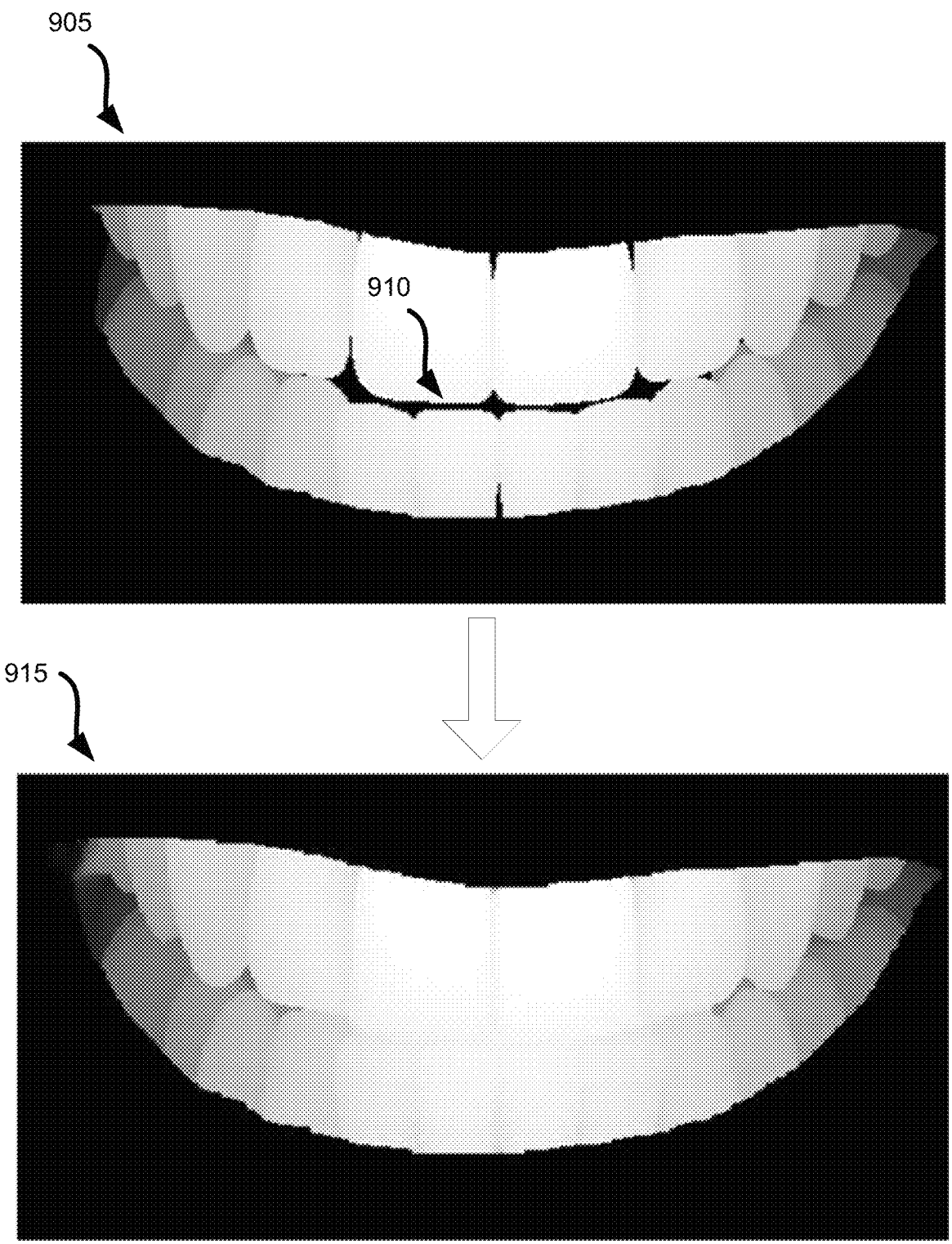
FIG. 9 illustrates image data of a patient smile before and after performing inpainting, in accordance with an embodiment.

At block 218, processing logic performs inpainting to fill in any identified gaps between teeth. The inpainting includes changing the color values of pixel locations associated with the identified gaps with color values of pixel locations associated with nearby teeth. FIG. 9 illustrates a 3D virtual model 905 that is a rendering of a 2D image with depth value information, where the 3D virtual model 905 includes gaps 910. FIG. 9 further illustrates an updated 3D virtual model 915 after performing inpainting to fill in the gaps 910.

Returning to FIGS. 2A-B, at block 220, processing logic determines from the first image a first region comprising a representation of teeth. The first region may include a first set of pixel locations (e.g., x and y coordinates for pixel locations) in the first image. The first region may be determined using a first mask of the first image in some embodiments, where the first mask identifies the first set of pixel locations of the first region that are associated with the teeth. The first mask may additionally identify pixel locations of a second region of the first image that is associated with gingiva.

In one embodiment, processing logic generates the first mask for the first image at block 222. The first mask may be generated based on user input identifying the first region and/or the second region. For example, a user may trace an outline of the teeth and an outline of the gingiva in the first image, and the first mask may be generated based on the traced outlines. In one embodiment, the first mask is generated automatically using one or more trained neural network (e.g., such as a deep neural network). For example, a first neural network may process the first image to determine a bounding box around the teeth and gingiva. The image data within the bounding box may then be processed using a second trained neural network and/or one or more image processing algorithms to identify the gingiva and/or teeth within the bounding box. This data may then be used to automatically generate the first mask without user input.

At block 224, processing logic determines depth values associated with one or more pixel locations in the first region (in the first set of pixel locations). In one embodiment, the depth values are determined from the virtual 3D model generated at block 212 (of the inpainted virtual 3D model at block 218). In one embodiment, processing logic generates a height map that assigns a height value (also referred to as a depth value) to each pixel location in the first set of pixel locations.

At block 225, processing logic generates a first function for a first color channel based on intensities of the color channel at the pixel locations in the first set of pixel locations as identified in the first mask. Processing logic may also generate a second parametric function for a second color channel, a third parametric function for a third color channel, and/or one or more additional parametric functions for additional color channels (for color spaces that have more than three channels). Any color space may be used for the color channels associated with the parametric functions. For example, a red-blue-green (RGB) color space may be used, in which a first function may be generated for the red color channel, a second parametric function may be generated for the blue color channel and a third parametric function may be generated for the green color channel. A non-exhaustive list of other example color spaces that may be used include the hue, saturation, value (HSV) color space, the hue, saturation, luminance (HSL) color space, the YUV color space, the LAB color space, and the cyan, magenta, yellow black (CMYK) color space. In some embodiments, a LAB color space is used to determine the height map, and is then converted to another color space (e.g., RGB) after the height map is generated. The height map may then be used across different color channels (e.g., may be used for functions associated with different color channels).

The parametric functions generated at block 225 are global blurring functions that may be used to generate blurred representations of teeth. Any of the aforementioned types of parametric and/or non-parametric functions may be used for the global blurring functions. Some examples of polynomial functions that may be used include first order polynomial functions, second order polynomial functions, third order polynomial functions, fourth order polynomial functions, and so on. Other types of parametric functions that may be used include trigonometric functions, exponential functions, fractional powers, and so on. The parametric functions may be smooth functions that vary in the x direction and/or in the y direction. For example, the parametric functions may vary in only the x direction, in only the y direction, or in both the x direction and the y direction. Examples of non-parametric functions include splines. The parametric functions and non-parametric functions are global functions that incorporate some local information.

Each function may be initially set up with unsolved coefficients or constant functions as in the case of non-parametric functions. Processing logic may then perform linear regression or back-fitting to solve for the values of the coefficients (also referred to as parameters) or the non-parametric functions using the intensity values of the pixel locations indicated by the mask as well as the depth information associated with the pixel locations.

A similar process as set forth above may also be used to generate a set of blurring functions for gingiva. Alternatively, a Gaussian blurring function may be used for gingiva (e.g., as set forth in equations 8-9 above).

At block 235, processing logic performs treatment simulation using the generated virtual 3D model. At block 238, processing logic generates a new 3D model based on the treatment simulation. One or more teeth may have a different position in the new 3D model than they did in the initial 3D model.

In some embodiments, the operations of blocks 235 and 238 are performed before the operations of block 225. In further embodiments, height map may be generated from the new virtual 3D model generated at lock 235, and this height map may be used at block 225 rather than a height map associated with the original virtual 3D model generated from the first image. In one embodiment, the first virtual 3D model is compared to the new virtual 3D model to determine pixel locations that are associated with teeth in both virtual 3D models. In one embodiment, pixel locations that are not in both the first virtual 3D model and the new virtual 3D model are discarded from the height map. The height map that is then used to generate the first function (and additional functions) may be solved for using the updated height map in which one or more pixel locations have been discarded.

At block 240, processing logic generates, from the new 3D model, image data comprising a new representation (e.g., contours) of the teeth in a second region. One or more of the teeth may have a different position in the image data than in the first image. The second region may comprise a second set of pixel locations for the teeth that is different than the first set of pixel locations. The first and second region may overlap (e.g., some pixel locations in the first set of pixel locations may also be in the set of second pixel locations). The image data may further comprise new depth values associated with pixel locations in the second set of pixel locations. In one embodiment, the depth information is represented in a height map that is generated and that accompanies and/or is included in the image data. The height map may specify depth values for one or more pixel locations in the second set of pixel locations.

The image data may be or include a 2D sketch of post-treatment dentition, a projection of a 3D virtual model of a dental arch into a 2D plane, or other image data. A 3D virtual model may be oriented such that the mapping of the 3D virtual model into the 2D plane results in a simulated 2D sketch of the teeth and gingiva from a same perspective from which the first image was taken in some embodiments. The 3D virtual model may be included in a treatment plan, and may represent a final shape of the upper and/or lower dental arches of a patient after treatment is complete. Alternatively, or additionally, one or more 2D sketches of post-treatment dentition may be included in the treatment plan, with or without a 3D virtual model of the dental arch. Alternatively, or additionally, one or more 2D sketches may be generated from a 3D template. The image data may be a line drawing that includes contours of the teeth and gingiva, but that lacks color data for one or more regions (e.g., a region associated with the teeth). In one embodiment, generating the image data comprises projecting the 3D virtual model of an upper and/or lower dental arch into a 2D plane.

In one embodiment, generating the image data comprises inferring a likely 3D structure from the first image, matching the 3D structure to a template for a dental arch (e.g., a template with an ideal tooth arrangement), and then projecting the template into 2D. The 3D template may be selected from a set of available 3D templates, and the 3D template may be a template having a dental arch that most closely matches a dental arch in the first image. The 3D template may be oriented such that the mapping of the 3D template into the 2D plane results in a 2D sketch of teeth and gingiva from a same perspective from which the first image was taken in some embodiments.

At block 242, processing logic determines the second region comprising the teeth in the image data. The second region comprising the teeth may comprise a second set of pixel locations for the teeth that is different than the first set of pixel locations. For example, a treatment plan may call for the repositioning of one or more teeth of the patient. The first image may show those teeth in their initial positions and/or orientations (e.g., which may include a malocclusion), and the image data may show those teeth in their final positions and/or orientations (e.g., in which a previous malocclusion may have been treated).

In one embodiment, processing logic generates a second mask for the image data at block 245. Processing logic may also generate another mask for the gingiva for the image data. The second mask may identify the second set of pixel locations associated with the new positions and/or orientations of the teeth. The other mask for the gingiva may indicate pixel locations for the upper and/or lower gingiva post treatment. The second mask (and optionally other mask) may be generated in the same manner as discussed above with regards to the first mask. In some embodiments, a 3D virtual model or 3D template includes information identifying teeth and gingiva. In such an embodiment, the second mask and/or other mask may be generated based on the information in the virtual 3D model or 3D template identifying the teeth and/or the gingiva.

At block 248, processing logic generates a blurred color representation of the teeth by applying the first function to the second set of pixel locations and the new depth values associated with the second set of pixel locations for the teeth that are identified in the second mask. This may include applying multiple different functions to pixel locations in the image data as specified in the second mask. For example, a first function for a first color channel may be applied to determine intensities or values of that first color channel for each pixel location associated with teeth, a second function for a second color channel may be applied to determine intensities or values of that second color channel for each pixel location associated with the teeth, and a third function for a third color channel may be applied to determine intensities or values of that third color channel for each pixel location associated with the teeth. The blurred color representation of the teeth may then include, for each pixel location associated with teeth in the image data, three different color values (or four different color channels for some color spaces), one for each color channel. A similar process may also be performed for the gingiva by applying one or more blurring functions to the pixel locations associated with the gingiva. Accordingly a single blurred color image may be generated that includes a blurred color representation of the teeth and a blurred color representation of the gingiva, where different blurring functions were used to generate the blurred color data for the teeth and gingiva.

At block 250, a new image is generated based on the image data (e.g., the sketch containing contours of the teeth and gingiva) and the blurred color image (e.g., which may contain a blurred color representation of the teeth and optionally a blurred color representation of the gingiva). A shape of the teeth in the new simulated image may be based on the image data and a color of the teeth (and optionally gingiva) may be based on the blurred color image containing the blurred color representation of the teeth and/or gingiva. In one embodiment, the new image is generated by inputting the image data and the blurred color image into an artificial neural network that has been trained to generate images from an input line drawing (sketch) and an input blurred color image. In one embodiment, the artificial neural network is a GAN. In one embodiment, the GAN is a picture to picture GAN.

Figure 3:
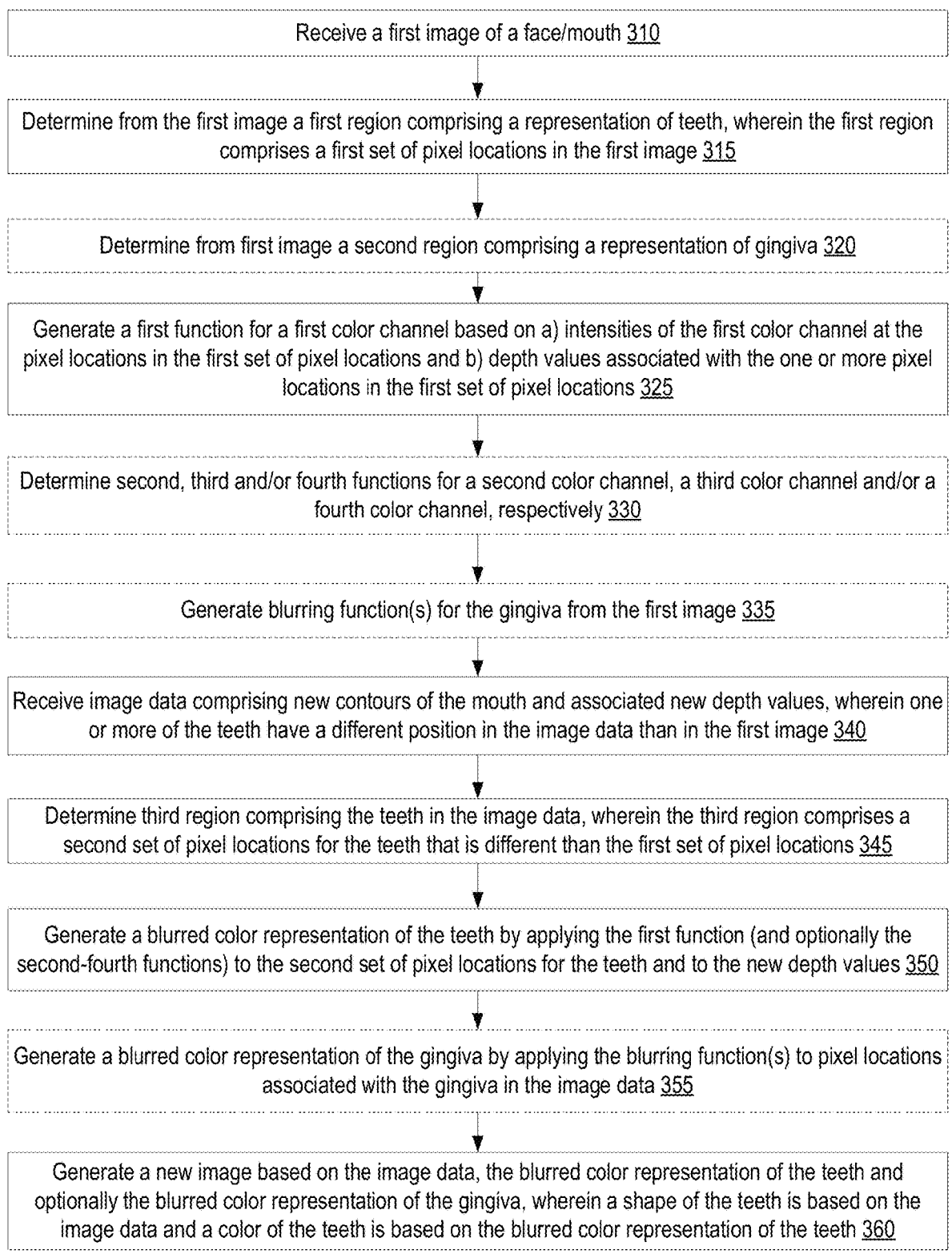
FIG. 3 also illustrates a flow diagram for a method of generating simulated images of dental treatment outcomes, in accordance with an embodiment.

FIG. 3 also illustrates a flow diagram for a method 300 of generating simulated images of dental treatment outcomes, in accordance with an embodiment. At block 310 of method 300, processing logic receives a first image of a patient's face and/or mouth. The image may be an image of the patient smiling with their mouth open such that the patient's teeth and gingiva are showing. The first image may be a two-dimensional (2D) color image in embodiments.

At block 315, processing logic determines from the first image a first region comprising a representation of teeth. The first region may include a first set of pixel locations (e.g., x and y coordinates for pixel locations) in the first image. At block 320, processing logic may determine from the first image a second region comprising a representation of gingiva. The second region may include a second set of pixel locations in the first image.

The first region may be determined using a first mask of the first image in some embodiments, where the first mask identifies the first set of pixel locations of the first region that are associated with the teeth. The second region may be determined using a second mask of the first image, where the second mask identifies the second set of pixel locations of the second region that are associated with the gingiva. In one embodiment, a single mask identifies the first region associated with the teeth and the second region associated with the gingiva. In one embodiment, processing logic generates the first mask and/or the second mask as described with reference to block 222 of method 200.

At block 325, processing logic generates a first function for a first color channel based a) on intensities (or other values) of the color channel at the pixel locations in the first set of pixel locations as identified in the first mask and b) depth values associated with the one or more pixel locations in the first set of pixel locations. In one embodiment, the depth values are determined from a height map that is generated by first generating a 3D virtual model of a dental arch from the 2D image and then determining z values of pixel locations in the 3D virtual model from a perspective associated with the 2D image.

At block 330, processing logic may also generate a second function for a second color channel, a third function for a third color channel, and/or one or more additional functions for additional color channels (for color spaces that have more than three channels). Any color space may be used for the color channels associated with the parametric functions. For example, a red-blue-green color space may be used, in which a first function may be generated for the red color channel, a second function may be generated for the blue color channel and a third function may be generated for the green color channel. A non-exhaustive list of other example color spaces that may be used include the hue, saturation, value (HSV) color space, the hue, saturation, luminance (HSL) color space, the YUV color space, the LAB color space, and the cyan, magenta, yellow black (CMYK) color space.

The functions generated at blocks 325 and 330 are global blurring functions that use x,y pixel locations as well as associated depth values that may be used to generate blurred representations of teeth. Any of the aforementioned types of functions may be used for the global blurring functions.

At block 335, blurring functions may be generated for the gingiva from the first image. In one embodiment, a set of functions is generated for the gingiva in the same manner as set forth above for the teeth. For example, a mask identifying pixel locations associated with gingiva may be used to identify the pixel locations to be used to solve for the parameters of one or more functions. Alternatively, a Gaussian blurring function may be used for the gingiva using the pixel locations associated with the gingiva.

At block 340, processing logic receives image data and/or generates image data comprising new contours of the mouth based on a treatment plan. The image data may be a projection of a 3D virtual model of a dental arch into a 2D plane. The 3D virtual model may be oriented such that the mapping of the 3D virtual model into the 2D plane results in a simulated 2D sketch of the teeth and gingiva from a same perspective from which the first image was taken in some embodiments. The 3D virtual model may be included in a treatment plan, and may represent a final shape of the upper and/or lower dental arches of a patient after treatment is complete. The image data may be a line drawing that includes contours of the teeth and gingiva, but that lacks color data. In one embodiment, generating the image data comprises projecting the 3D virtual model of an upper and/or lower dental arch into a 2D plane. Processing logic may also generate or receive a height map that comprises new depth values associated with the second set of pixel locations. The height map may be included in the image data in embodiments.

At block 345, processing logic determines a third region comprising the teeth in the image data. The third region comprising the teeth may comprise a second set of pixel locations for the teeth that is different than the first set of pixel locations. In one embodiment, processing logic generates a second mask for the image data, and the second mask is used to determine the third region.

At block 350, processing logic generates a blurred color representation of the teeth by applying the first function and optionally the second, third and/or fourth functions to the second set of pixel locations for the teeth that are associated with the third region and to the new depth values. The blurred color representation of the teeth may then include, for each pixel location associated with teeth in the image data, three (or four) different color values, one for each color channel. The third region of the image data may have more or fewer pixels than the first region of the first image. The function works equally well whether the third region has fewer pixels, the same number of pixels, or a greater number of pixels.

At block 355, processing logic may generate a blurred color representation of the gingiva by applying the one or more blurring functions for the gingiva to pixel locations (and optionally depth values) associated with the gingiva in the image data. The blurred color representation of the teeth may be combined with the blurred color representation of the gingiva to generate a single blurred color image.

At block 360, a new image is generated based on the image data (e.g., the sketch containing contours of the teeth and gingiva) and the blurred color image (e.g., which may contain a blurred color representation of the teeth and optionally a blurred color representation of the gingiva). A shape of the teeth in the new simulated image may be based on the image data and a color of the teeth (and optionally gingiva) may be based on the blurred color image containing the blurred color representation of the teeth and/or gingiva. In one embodiment, the new image is generated by inputting the image data and the blurred color image into an artificial neural network that has been trained to generate images from an input line drawing (sketch) and an input blurred color image. In one embodiment, the artificial neural network is a GAN. In one embodiment, the GAN is a picture to picture GAN.

In some instances the lower gingiva may not be visible in the first image, but may be visible in the new simulated image that is generated at block 360. In such instances, functions generated for the use of blurring the color data for the gingiva may cause the coloration of the lower gingiva to be inaccurate. In such instances, one or more Gaussian blurring functions may be generated for the gingiva at block 335.

Figure 4:
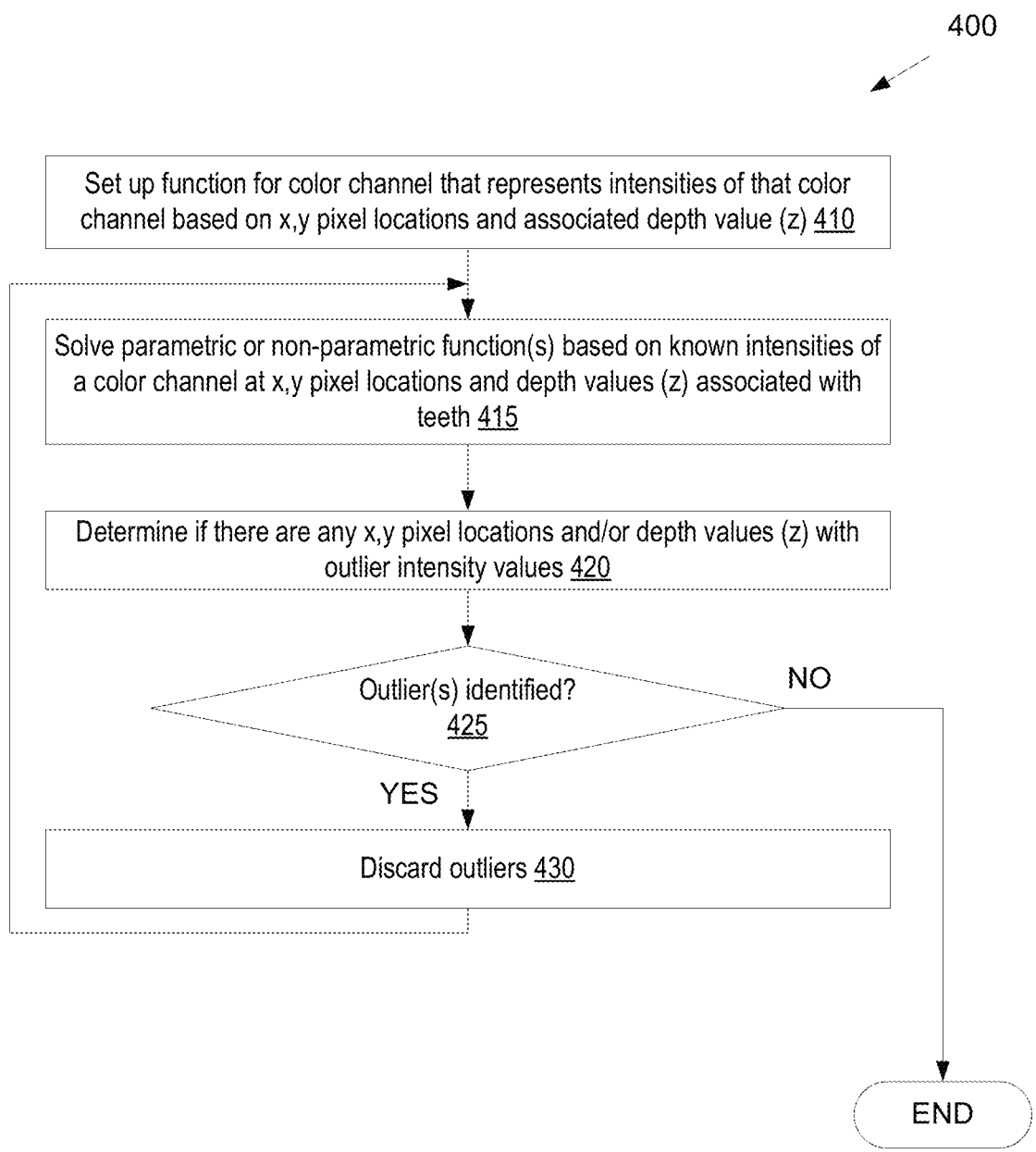
FIG. 4 illustrates a flow diagram for a method of generating a parametric or non-parametric color blurring function, in accordance with an embodiment.

FIG. 4 illustrates a flow diagram for a method 400 of generating a parametric or non-parametric color blurring function, in accordance with an embodiment. Method 400 may be performed for each blurring function that will be generated for an image. For example, if functions will be used to generate both blurred color representations of teeth and gingiva, then six or eight total parametric blurring functions may be set up, where 3-4 of the parametric functions are set up for the various color channels associated with teeth and 3-4 of the parametric functions are set up for the various color channels associated with the gingiva.

At block 410 of method 400, processing logic sets up a function for a color channel that represents intensities (or other values) of that color channel based on x,y pixel location and depth (z) values. Setting up the function may include generating an unsolved function for which the coefficients associated with the terms of the parametric function are unknown or the function shape is unknown in the case of non-parametric functions.

At block 415, processing logic solves the function based on known intensities (or other values) of the color channel at all or a subset of the x,y,z pixel locations associated with teeth (or the x,y,z pixel locations associated with gingiva if the function will be used for gingiva). The function may be solved by performing regression or back-fitting as discussed above. An initial image (e.g., as generated by a camera or image sensor) may include representations of teeth, and a mask may identify those pixel locations that are associated with representations of teeth. A 3D model may be generated from the initial image, a treatment planning simulation may be performed on the 3D model, and a new 3D model may be generated from the treatment planning simulation. A height map may be generated from the initial 3D model or from the new 3D model. The height map may associate a depth (z) value with each x,y pixel location. Accordingly, the x,y,z pixel locations for teeth and the color values for a particular color channel at those x,y,z pixel locations are known. This information can be used to solve for the weights in the function by performing multiple linear regression or back-fitting.

In some embodiments, one or more outlier rejection techniques are used to generate functions that are a better fit to the color data of the teeth (or gingiva) in the first image. In one embodiment, at block 420 processing logic determines if there are any x,y,z pixel locations with outlier intensity values for the color channel. Examples of outlier detection techniques that may be used to detect (and optionally reject) outliers include z-score, standard deviation, density based spatial clustering of applications with noise (Dbscan) and isolation forests. For example, processing logic may determine for each x,y,z pixel location an intensity for the color channel specified by the parametric function and compare that intensity value to an actual measured intensity value at that x,y,z pixel location. Processing logic may determine whether a difference between the two intensity values exceeds a difference threshold. The difference threshold may be set, for example, based on a standard deviation of the differences between measured and predicted intensity values. If the difference exceeds a difference threshold, then at block 420 processing logic may identify an outlier. If an outlier is identified, then processing logic discards the outlier (or multiple outliers) at block 430.

The method may then return to block 415 and the function may be solved again using the remaining pixel locations. This process may be repeated until no new outliers are identified. If at block 425 no new outliers are identified, then the method ends.

In one embodiment, the random sample consensus (RANSAC) is used to determine an optimal function that fits the data. Other related techniques that may be used include maximum likelihood estimate sample consensus (MLE-SAC) and maximum a posterior sample consensus (MAP-SAC). The outlier rejection technique or techniques may be applied so as to discard color data for teeth that might be discolored (e.g., black or gray). Such color data for the discolored teeth could negatively impact the functions and cause the coloration of other teeth to be inaccurate. Accordingly, the outlier rejection technique(s) such as RANSAC may be applied on the fit to improve the ultimate blurred color representation of the teeth.

Figure 5:
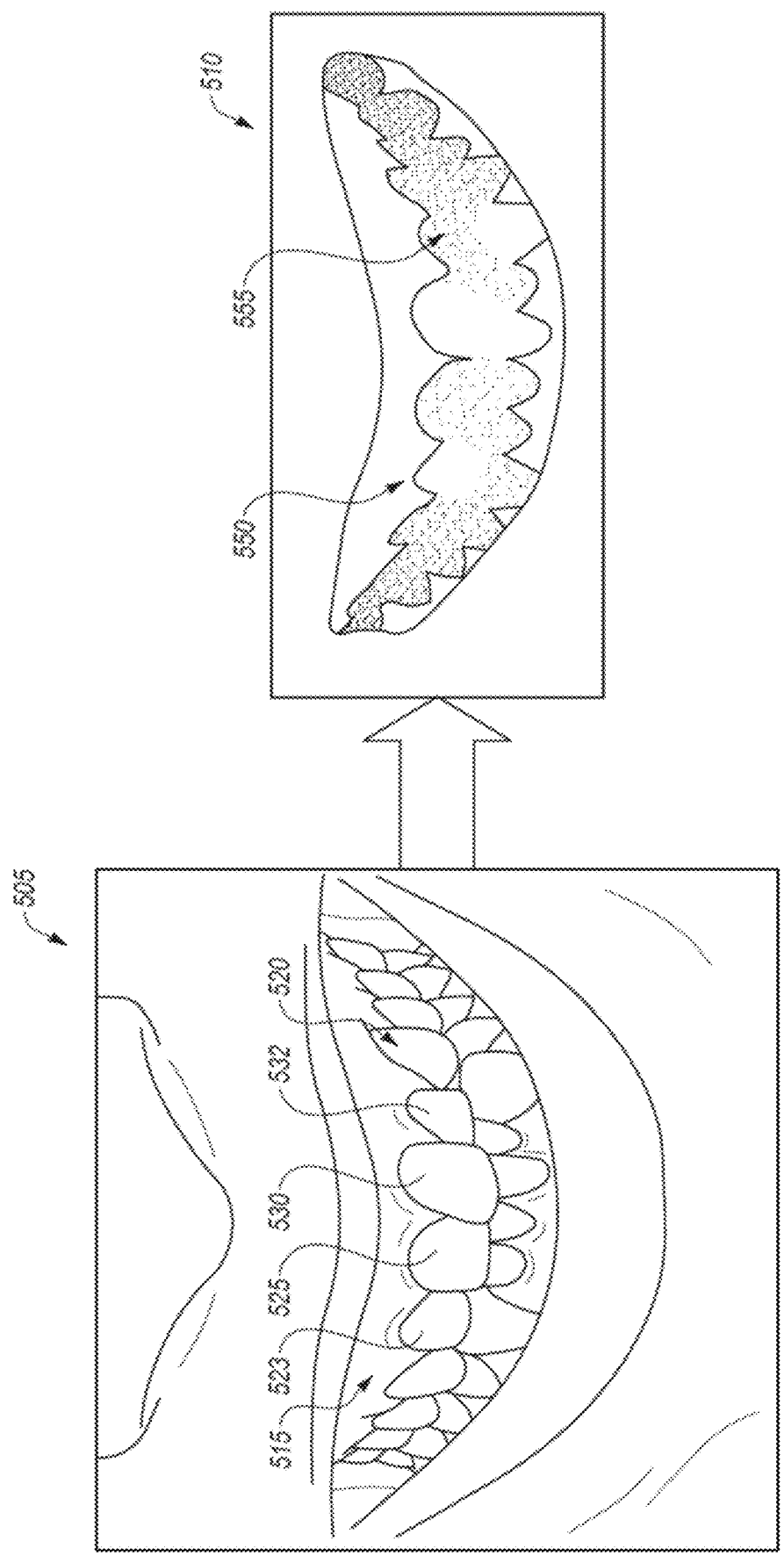
FIG. 5 illustrates an image of a patient smile and a blurred representation of the teeth and gingiva from the image, in accordance with an embodiment.
Figure 6:
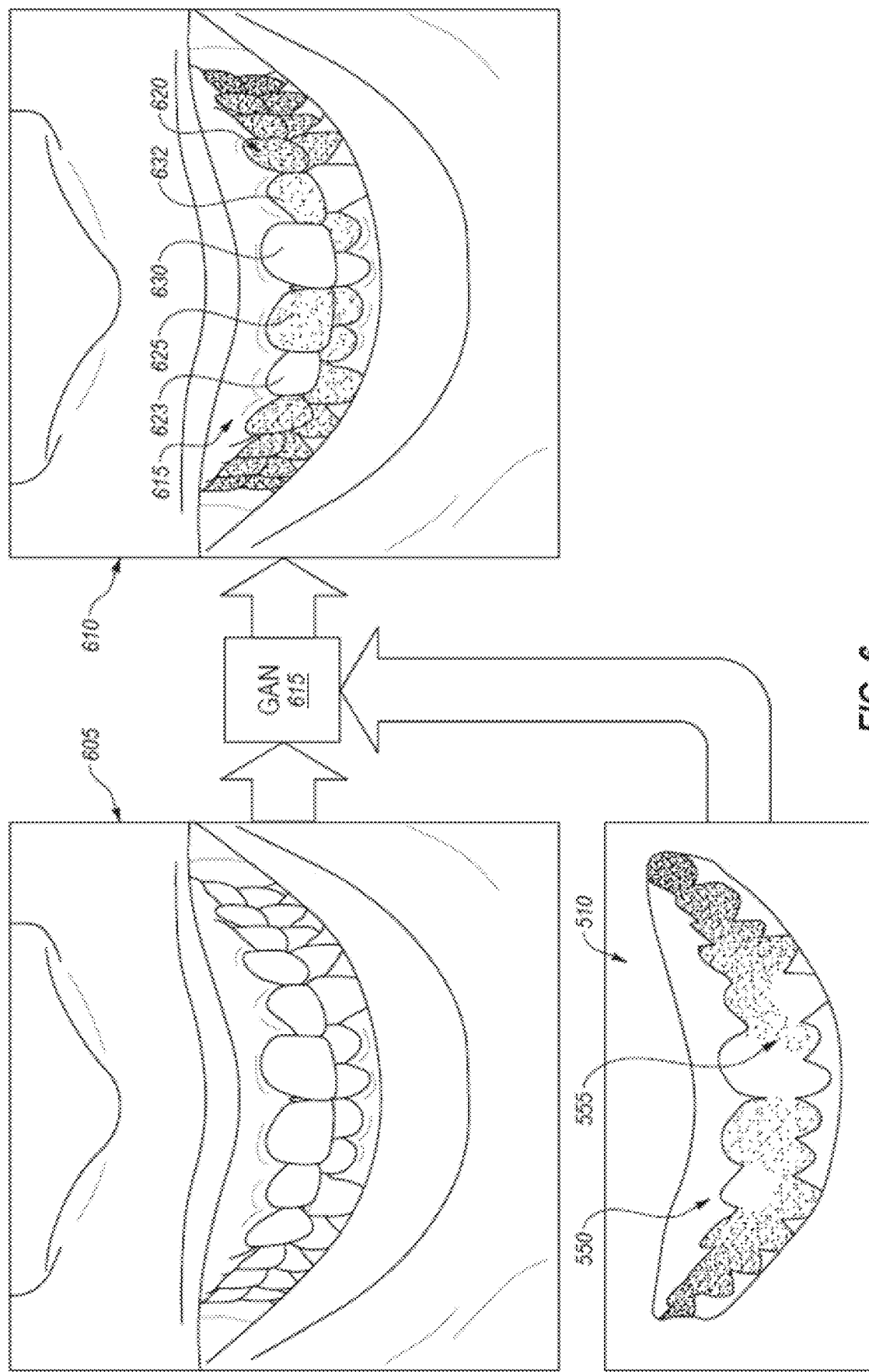
FIG. 6 illustrates a simulated image of a post-treatment patient smile as generated by a neural network based on a first input of image data representing post-treatment teeth and gingiva contours and a second input of a blurred representation of the teeth and gingiva, in accordance with one embodiment.

FIGS. 5-6 depict use of a local blurring function (e.g., a Gaussian blurring function) to generate a simulated image of a post-treatment smile based on an initial image of a pre-treatment smile. FIG. 5 illustrates an image 505 of a patient smile and a blurred color image 510 including a blurred color representation of the teeth 555 and a blurred color representation of the gingiva 550 from the image 505, in accordance with an embodiment. As shown, image 505 includes gingiva 515 and teeth 520. In the image 505, the maxillary lateral left incisor 523 is prominent and the maxillary lateral right incisor 532 is recessed and in shadow. Similarly, the maxillary central left incisor 525 is recessed and the maxillary central right incisor 530 is prominent. This arrangement of teeth causes the maxillary lateral left incisor 523 and the maxillary central right incisor 530 to be brighter than the maxillary lateral right incisor 532 and the maxillary central left incisor 525. The blurred color image 510 generated from the image 505 using Gaussian blurring does not have structural data, but does have bright spots associated with the locations of the maxillary lateral left incisor 523 and the maxillary central right incisor 530 and dark spots associated with the locations of the maxillary lateral right incisor 532 and the maxillary central left incisor 525.

FIG. 6 illustrates a simulated image 610 of a post-treatment patient smile as generated by a neural network 615 based on a first input of image data 605 representing post-treatment teeth and gingiva contours and a second input of a blurred color image 510 that includes a blurred color representation of the teeth 555 and a blurred color representation of the gingiva 550, in accordance with one embodiment. As shown, the blurred color image 510 includes the aforementioned dark spots and bright spots. This causes the neural network (e.g., a picture to picture GAN) 615 to generate a simulated image 610 of a post treatment smile including gingiva 615 and teeth 620 in which the maxillary lateral left incisor 623 is brighter than the maxillary lateral right incisor 632 and in which the maxillary central right incisor 630 is brighter than the maxillary central left incisor 625.

Figure 7:
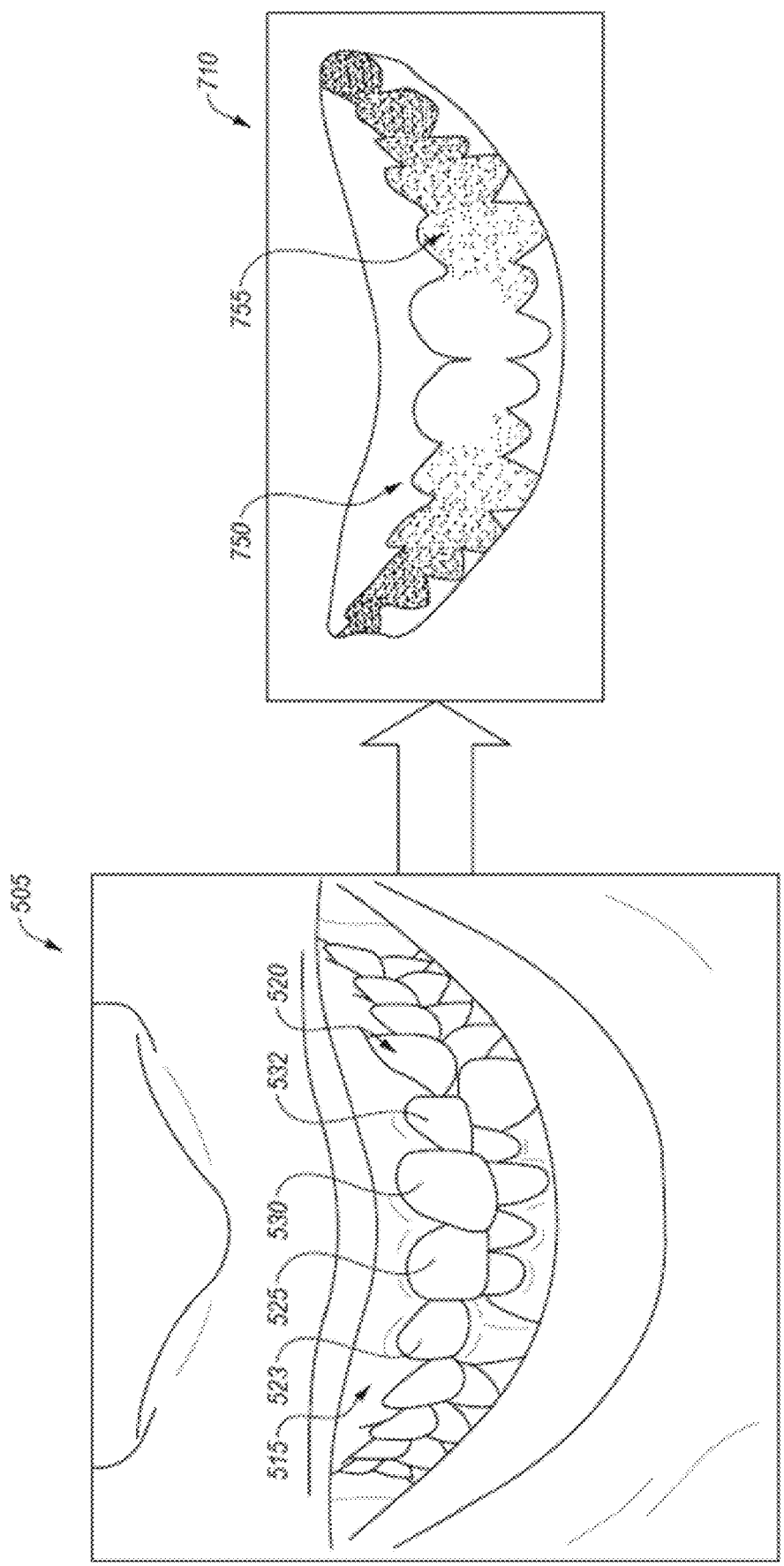
FIG. 7 illustrates an image of a patient smile and a blurred representation of the teeth and gingiva from the image, in accordance with an embodiment.
Figure 8:
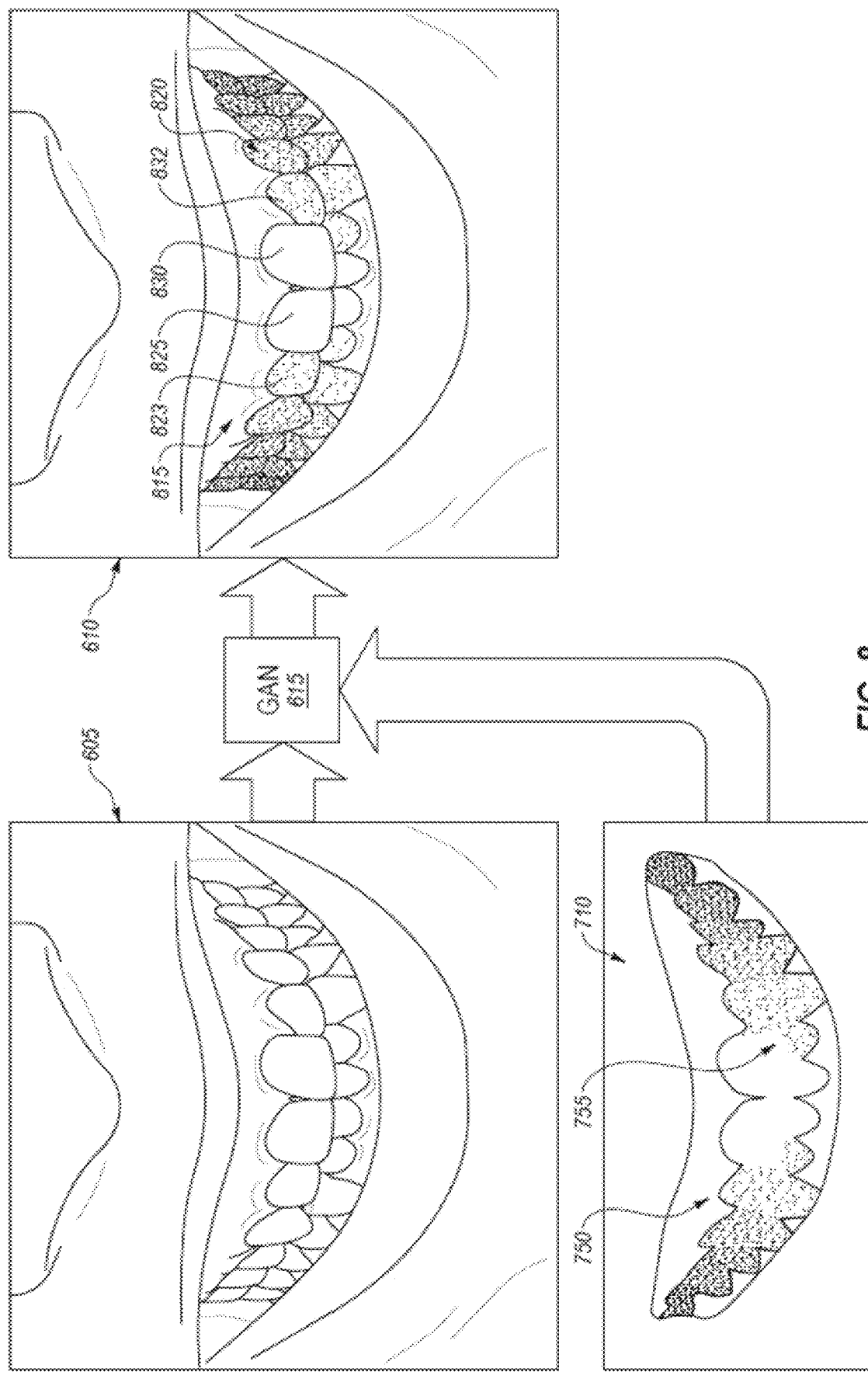
FIG. 8 illustrates a simulated image of a post-treatment patient smile as generated by a neural network based on a first input of image data representing post-treatment teeth and gingiva contours and a second input of a blurred representation of the teeth and gingiva, in accordance with one embodiment.

FIGS. 7-8 depict use of a global blurring function (e.g., a parametric or non-parametric blurring function) to generate a simulated image of a post-treatment smile based on an initial image of a pre-treatment smile. FIG. 7 illustrates the image 505 of a patient smile shown in FIG. 5 and a blurred color image 710 including a blurred color representation of the teeth 755 and a blurred color representation of the gingiva 750 from the image 505, in accordance with an embodiment. However, in contrast to the blurred color image 510 of FIG. 5, the blurred color image 710 is generated using parametric or non-parametric blurring functions, where the blurring functions were generated using pixel locations of teeth in the image 505 and associated depth information. As shown, the blurred color representation of the teeth 755 has approximately the same intensity and color for the areas associated with the maxillary central left incisor 525 and the maxillary central right incisor 530. Similarly, the blurred color representation of the teeth 755 has approximately the same intensity and color for the areas associated with the maxillary lateral left incisor 523 and the maxillary lateral right incisor 532.

FIG. 8 illustrates a simulated image 810 of a post-treatment patient smile as generated by a neural network 615 based on a first input of image data 605 representing post-treatment teeth and gingiva contours and a second input of a blurred color image 710 comprising a blurred color representation of the teeth 755 and a blurred color representation of the gingiva 750, in accordance with one embodiment. As shown, the blurred color image 710 includes an approximately smooth transition from light colors/intensities at the central incisors to dark colors/intensities at the molars. This causes the neural network (e.g., a picture to picture GAN) 615 to generate a simulated image 810 of a post treatment smile including gingiva 815 and teeth 820 in which the maxillary lateral left incisor 823 has approximately a same intensity as the maxillary lateral right incisor 832 and in which the maxillary central right incisor 830 has approximately the same intensity as the maxillary central left incisor 825. Accordingly, the blurred color image that has been generated using parametric or non-parametric blurring functions that are based on x,y pixel locations as well as depth (z) can be used along with image data (e.g., a sketch or contours of a final position of teeth) as inputs into an artificial neural network 615 to enable the artificial neural network 615 to generate a simulated image 810 that has accurate texture data that more closely corresponds to the colors that the teeth would have after treatment.

Figure 14:
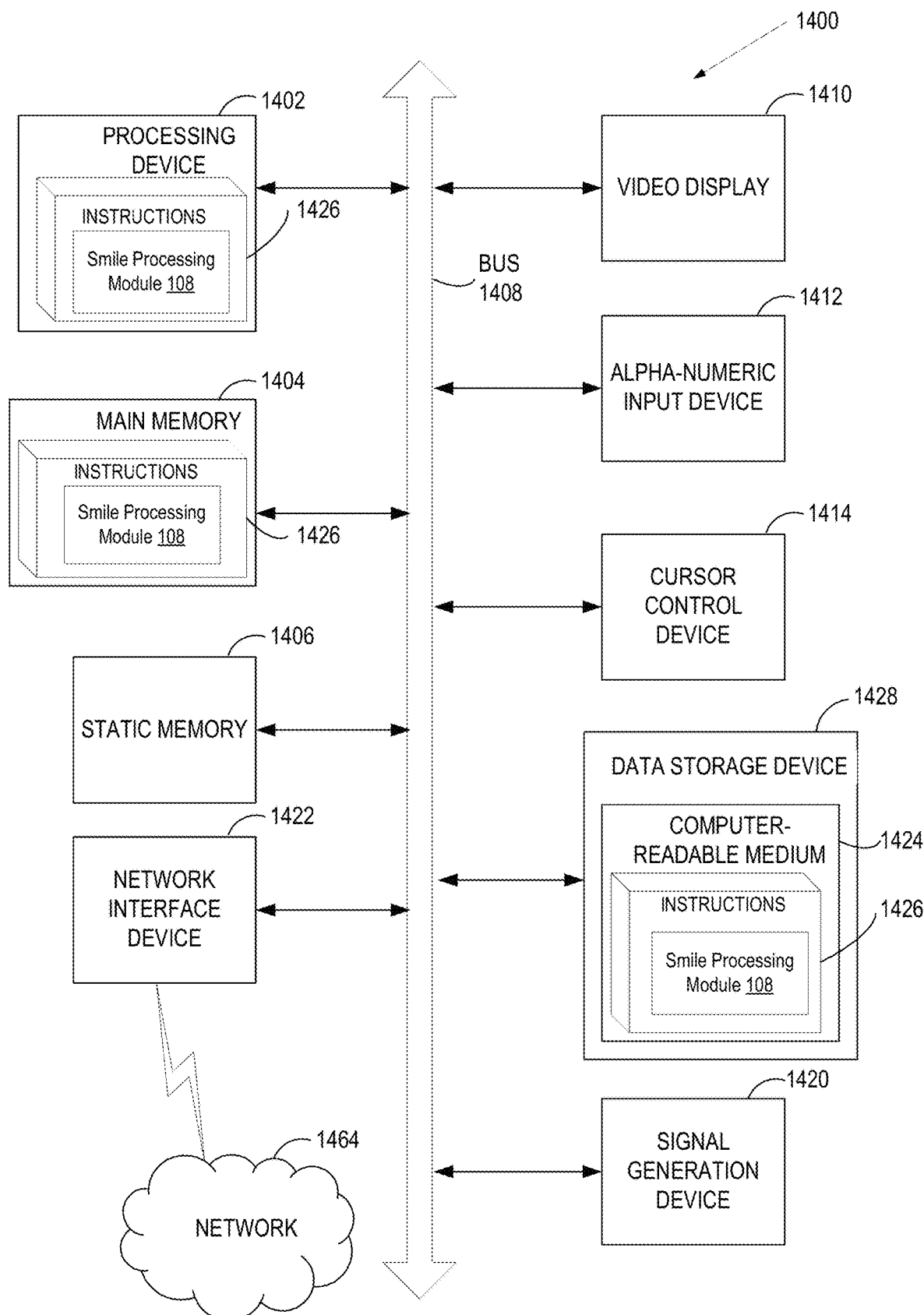
FIG. 14 illustrates a block diagram of an example computing device, in accordance with embodiments of the present disclosure.

FIG. 14 illustrates a diagrammatic representation of a machine in the example form of a computing device 1400 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a personal digital assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computer device 1400 corresponds to computing device 105 of FIG. 1.

The example computing device 1400 includes a processing device 1402, a main memory 1404 (e.g., read-only memory (ROM), flash memory, dynamic random access memory (DRAM) such as synchronous DRAM (SDRAM), etc.), a static memory 1406 (e.g., flash memory, static random access memory (SRAM), etc.), and a secondary memory (e.g., a data storage device 1428), which communicate with each other via a bus 1408.

Processing device 1402 represents one or more general-purpose processors such as a microprocessor, central processing unit, or the like. More particularly, the processing device 1402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1402 may also be one or more special-purpose processing devices such as an application specific integrated circuit (ASIC), a field programmable gate array (FPGA), a digital signal processor (DSP), network processor, or the like. Processing device 1402 is configured to execute the processing logic (instructions 1426) for performing operations and steps discussed herein.

The computing device 1400 may further include a network interface device 1422 for communicating with a network 1464. The computing device 1400 also may include a video display unit 1410 (e.g., a liquid crystal display (LCD) or a cathode ray tube (CRT)), an alphanumeric input device 1412 (e.g., a keyboard), a cursor control device 1414 (e.g., a mouse), and a signal generation device 1420 (e.g., a speaker).

The data storage device 1428 may include a machine-readable storage medium (or more specifically a non-transitory computer-readable storage medium) 1424 on which is stored one or more sets of instructions 1426 embodying any one or more of the methodologies or functions described herein, such as instructions for a smile processing module 108. A non-transitory storage medium refers to a storage medium other than a carrier wave. The instructions 1426 may also reside, completely or at least partially, within the main memory 1404 and/or within the processing device 1402 during execution thereof by the computer device 1400, the main memory 1404 and the processing device 1402 also constituting computer-readable storage media.

The computer-readable storage medium 1424 may also be used to store a smile processing module 108. The computer readable storage medium 1424 may also store a software library containing methods for a smile processing module 108. While the computer-readable storage medium 1424 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method comprising:
   determining, from a first image of a mouth, a first region of the first image comprising a representation of teeth, wherein the first region comprises a first set of pixel locations in the first image;
   determining depth values associated with one or more of pixel locations in the first set of pixel locations;
   generating a first function for a first color channel based on a) intensities of the first color channel at the one or more pixel locations in the first set of pixel locations and b) depth values associated with the one or more pixel locations in the first set of pixel locations, wherein the first function comprises a first variable for a first image axis, a second variable for a second image axis and a third variable for a third image axis;
   receiving image data comprising a new representation of the teeth in a second region, wherein one or more of the teeth have a different position in the image data than in the first image, wherein the second region comprises a second set of pixel locations for the teeth that is different than the first set of pixel locations, and wherein the image data further comprises new depth values associated with pixel locations in the second set of pixel locations; and
   generating a new image based on the image data and the first function, wherein a shape of the teeth is based on the image data and a color of the teeth is based on applying the first function to the second set of pixel locations for the teeth and the new depth values associated with the second set of pixel locations for the teeth.

2. The method of claim 1, further comprising:
   generating a first mask for the first image, wherein the first mask identifies the first set of pixel locations of the first region that are associated with the teeth;
   generating a second mask for the image data; and
   determining the second region comprising the teeth in the image data using the second mask, wherein the second mask identifies the second set of pixel locations of the second region that are associated with the teeth.

3. The method of claim 1, wherein regions of the image data lack color data for the teeth.

4. The method of claim 1, further comprising:
   receiving the first image, wherein the first image was generated by an image sensor;
   generating a three-dimensional (3D) model from the first image;
   determining the depth values associated with one or more of pixel locations in the first set of pixel locations from the 3D model.

5. The method of claim 4, wherein the first image is a two-dimensional (2D) image, the method further comprising:
   performing a treatment simulation using the 3D model;

generating a new 3D model based on the treatment simulation, where the one or more of the teeth have the different position in the new 3D model; and generating the image data based on the new 3D model, wherein the image data is 2D image data.

6. The method of claim 4, further comprising:
identifying a gap between two adjacent teeth; and
performing inpainting to fill in the gap between the two adjacent teeth with a color based on a color of a point on at least one of the two adjacent teeth.

7. The method of claim 1, further comprising:
generating a second function for a second color channel based on a) intensities of the second color channel at the pixel locations in the first set of pixel locations and b) depth values associated with the one or more pixel locations in the first set of pixel locations; and
generating a third function for a third color channel based on a) intensities of the third color channel at the pixel locations in the first set of pixel locations and b) depth values associated with the one or more pixel locations in the first set of pixel locations;
wherein the color of the teeth is further based on a) applying the second function to the second set of pixel locations for the teeth and the new depth values associated with the second set of pixel locations for the teeth and b) applying the third function to the second set of pixel locations for the teeth and the new depth values associated with the second set of pixel locations for the teeth.

8. The method of claim 1, wherein the first function comprises a first sub-function f(x,y) for x,y pixel locations and a second sub-function g(z) for depth values.

9. The method of claim 8, wherein the first function comprises an additive or multiplicative combination of the first sub-function and the second sub-function, and wherein the first sub-function and the second sub-function are parametric functions, the method further comprising:
performing linear regression to solve for parameters of the first function.

10. The method of claim 8, wherein the first function comprises an additive or multiplicative combination of the first sub-function and the second sub-function, and wherein at least one of the first sub-function or the second sub-function is a non-parametric function, the method further comprising:
performing back fitting to solve for functional forms of the first function.

11. The method of claim 1, further comprising:
generating a blurred color representation of the teeth by applying the first function to the second set of pixel locations for the teeth and the new depth values associated with the second set of pixel locations for the teeth; and
processing the blurred color representation of the teeth and the received image data by a neural network to generate the new image.

12. A computer readable storage medium comprising instructions that, when executed by a processing device, cause the processing device to perform operations comprising:
determining, from a first image of a mouth, a first region of the first image comprising a representation of teeth, wherein the first region comprises a first set of pixel locations in the first image;
determining depth values associated with one or more of pixel locations in the first set of pixel locations;
generating a first function for a first color channel based on a) intensities of the first color channel at the one or more pixel locations in the first set of pixel locations and b) depth values associated with the one or more pixel locations in the first set of pixel locations, wherein the first function comprises a first variable for a first image axis, a second variable for a second image axis and a third variable for a third image axis;
receiving image data comprising a new representation of the teeth in a second region, wherein one or more of the teeth have a different position in the image data than in the first image, wherein the second region comprises a second set of pixel locations for the teeth that is different than the first set of pixel locations, and wherein the image data further comprises new depth values associated with pixel locations in the second set of pixel locations; and
generating a new image based on the image data and the first function, wherein a shape of the teeth is based on the image data and a color of the teeth is based on applying the first function to the second set of pixel locations for the teeth and the new depth values associated with the second set of pixel locations for the teeth.

13. The computer readable storage medium of claim 12, wherein the instructions further cause the processing device to perform operations comprising:
generating a first mask for the first image, wherein the first mask identifies the first set of pixel locations of the first region that are associated with the teeth;
generating a second mask for the image data; and
determining the second region comprising the teeth in the image data using the second mask, wherein the second mask identifies the second set of pixel locations of the second region that are associated with the teeth.

14. The computer readable storage medium of claim 12, wherein the instructions further cause the processing device to perform operations comprising:
receiving the first image, wherein the first image was generated by an image sensor;
generating a three-dimensional (3D) model from the first image; and
determining the depth values associated with one or more of pixel locations in the first set of pixel locations from the 3D model.

15. The computer readable storage medium of claim 14, wherein the first image is a two-dimensional (2D) image, and wherein the instructions further cause the processing device to perform operations comprising:
performing a treatment simulation using the 3D model;
generating a new 3D model based on the treatment simulation, where the one or more of the teeth have the different position in the new 3D model; and
generating the image data based on the new 3D model, wherein the image data is 2D image data.

16. The computer readable storage medium of claim 12, wherein the instructions further cause the processing device to perform operations comprising:
generating a second function for a second color channel based on a) intensities of the second color channel at the pixel locations in the first set of pixel locations and b) depth values associated with the one or more pixel locations in the first set of pixel locations; and
generating a third function for a third color channel based on a) intensities of the third color channel at the pixel locations in the first set of pixel locations and b) depth values associated with the one or more pixel locations in the first set of pixel locations;

wherein the color of the teeth is further based on a) applying the second function to the second set of pixel locations for the teeth and the new depth values associated with the second set of pixel locations for the teeth and b) applying the third function to the second set of pixel locations for the teeth and the new depth values associated with the second set of pixel locations for the teeth.

17. The computer readable storage medium of claim 12, wherein the first function comprises a first sub-function f(x,y) for x,y pixel locations and a second sub-function g(z) for depth values.

18. The computer readable storage medium of claim 17, wherein the first function comprises an additive or multiplicative combination of the first sub-function and the second sub-function, and wherein the first sub-function and the second sub-function are parametric functions, the operations further comprising:

performing linear regression to solve for parameters of the first function.

19. The computer readable storage medium of claim 17, wherein the first function comprises an additive or multiplicative combination of the first sub-function and the second sub-function, and wherein at least one of the first sub-function or the second sub-function is a non-parametric function, the operations further comprising:

performing back fitting to solve for parameters of the first function.

20. The computer readable storage medium of claim 12, the operations further comprising:

generating a blurred color representation of the teeth by applying the first function to the second set of pixel locations for the teeth and the new depth values associated with the second set of pixel locations for the teeth; and processing the blurred color representation of the teeth and the received image data by a neural network to generate the new image, wherein the neural network is a pixel to pixel generative adversarial network that was trained using a training dataset comprising a plurality of images of smiles.

21. A system comprising:

a memory device; and a processing device operatively coupled to the memory device, the processing device to:

determine, from a first image of a mouth, a first region of the first image comprising a representation of teeth, wherein the first region comprises a first set of pixel locations in the first image;

determine depth values associated with one or more of pixel locations in the first set of pixel locations;

generate a first function for a first color channel based on a) intensities of the first color channel at the one or more pixel locations in the first set of pixel locations and b) depth values associated with the one or more pixel locations in the first set of pixel locations, wherein the first function comprises a first variable for a first image axis, a second variable for a second image axis and a third variable for a third image axis;

receive image data comprising a new representation of the teeth in a second region, wherein one or more of the teeth have a different position in the image data than in the first image, wherein the second region comprises a second set of pixel locations for the teeth that is different than the first set of pixel locations, and wherein the image data further comprises new depth values associated with pixel locations in the second set of pixel locations; and generate a new image based on the image data and the first function, wherein a shape of the teeth is based on the image data and a color of the teeth is based on applying the first function to the second set of pixel locations for the teeth and the new depth values associated with the second set of pixel locations for the teeth.

* * * * *